United States Patent
Fujita et al.

(10) Patent No.: US 6,858,565 B2
(45) Date of Patent: Feb. 22, 2005

(54) THERMOSENSITIVE RECORDING MATERIAL AND NOVEL COLOR DEVELOPER COMPOUNDS

(75) Inventors: Hirotake Fujita, Kawasaki (JP); Jun-Ya Kojima, Chiba (JP); Ayako Shirai, Yokohama (JP); Yoshiyuki Takahashi, Tokyo (JP)

(73) Assignee: Oji Paper Co., Ltd., Tokyo (JP)

( * ) Notice: Subject to any disclaimer, the term of this patent is extended or adjusted under 35 U.S.C. 154(b) by 228 days.

(21) Appl. No.: 10/144,741

(22) Filed: May 13, 2002

(65) Prior Publication Data

US 2003/0040434 A1 Feb. 27, 2003

(30) Foreign Application Priority Data

| May 14, 2001 | (JP) | ........................................ | 2001-142696 |
| Jul. 12, 2001 | (JP) | ........................................ | 2001-212217 |
| Aug. 14, 2001 | (JP) | ........................................ | 2001-246198 |
| Dec. 12, 2001 | (JP) | ........................................ | 2001-378605 |

(51) Int. Cl.$^7$ .............................................. B41M 5/30
(52) U.S. Cl. ...................... 503/209; 503/214; 503/216; 503/225
(58) Field of Search ................................ 503/209, 214, 503/216, 225

(56) References Cited

U.S. PATENT DOCUMENTS

| 5,246,906 A | 9/1993 | Takahashi et al. |
| 5,256,618 A | 10/1993 | Takahashi et al. |

FOREIGN PATENT DOCUMENTS

| EP | 60-78782 | 5/1985 |
| EP | 0 526 072 A1 | 2/1993 |
| EP | 0 620 122 A1 | 10/1994 |
| EP | 1 044824 A2 | 10/2000 |
| JP | 56-146796 | 11/1981 |
| JP | 62-164579 | 7/1987 |
| JP | 62-169681 | 7/1987 |
| JP | 63-153183 | 6/1988 |
| JP | HEI5-32601 | 2/1993 |
| JP | HEI5-147357 | 6/1993 |
| JP | HEI6-1069 | 1/1994 |
| JP | HEI7-257033 | 10/1995 |
| JP | HEI8-333329 | 12/1996 |

*Primary Examiner*—N. Edwards
(74) *Attorney, Agent, or Firm*—Christie, Parker & Hale, LLP

(57) ABSTRACT

Disclosed is a thermosensitive recording material comprising a sheet-shaped support and a thermosensitive recording layer which is formed on at least one surface of the support and comprises a colorless or light-colored dye precursor and a color developer capable of reacting with the dye precursor and inducing color formation therein upon application of heat thereto, the color developer comprising a compound represented by the following formula (I) or analog thereof:

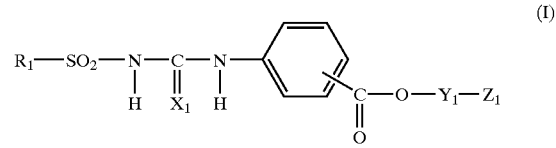

(I)

The thermosensitive recording material has high sensitivity and can prevent white background portions from coloring and recorded images from decolorizing in an environmental resistance test.

11 Claims, No Drawings

THERMOSENSITIVE RECORDING MATERIAL AND NOVEL COLOR DEVELOPER COMPOUNDS

BACKGROUND OF THE INVENTION

The present invention relates to a thermosensitive recording material that can produce colored images therein by the application of heat, and further to a thermosensitive recording material that can exhibit high whiteness degree and excellent preservation stability of recording.

In general, a thermosensitive recording material comprises a support such as a sheet of paper or synthetic paper or a plastic film and a thermosensitive coloring layer formed on the support. The thermosensitive coloring layer comprises as the main components a coloring material such as electron-donating leuco dyes and a color developer, that is, an organic acidic material such as phenol compounds. The coloring material and the color developer are caused to react upon the application of heat energy thereto to produce recorded images. Such thermosensitive recording materials, which are disclosed in, for example, Japanese Patent Publications 43-4160, 45-14039 and 48-27736, have been widely put to practical use.

The thermosensitive recording material is used in a wide variety of fields, for example, for use with the output of an electronic calculator, a facsimile machine, an automatic ticket vending machine, a printer for scientific measuring equipment, and a printer for CRT medical equipment. This is because the thermosensitive recording material has the advantages that the recording apparatus therefor is compact, inexpensive, and simple in maintenance. However, it is known that colored images decolorize with time in the above-mentioned conventional dye-containing thermosensitive recording material prepared by providing a thermosensitive coloring layer comprising a coloring dye material, a color developer, and a binder agent as the effective components on a support. The reason for this is that the coloring reaction is reversible. Such de-colorization is accelerated by the exposure to light, high humidity, and high temperature. Further, the de-colorization proceeds more quickly to such an extent that the colored images cannot be read when the colored images are allowed to stand in water for a long time, or brought into contact with oils such as salad oil and plasticizers.

In addition, the above-mentioned dye-containing thermosensitive recording material spontaneously causes the coloring reaction when stored under the circumstances of high temperature and humidity, which coloring reaction is called coloring of background, because the recording material has the properties that the coloring reaction takes place by the application of heat to the recording material. Such coloring reaction of the background will decrease the contrast, so that the recorded images become illegible. The background causes a noticeable coloring reaction to make the recorded images illegible, in particular, when thermosensitive recording type parking tickets and passes are allowed to stand in vehicles under the blazing sun in summer, or when thermosensitive recording type POS labels attached to the packages of cooked food and packaged lunch boxes sold in supermarkets or convenience stores are heated in the microwave.

There are disclosed a variety of methods for reducing the above-mentioned decolorizing phenomenon, using a dye-containing coloring system comprising as a main component a colorless or light-colored lactone ring compound (e.g. in Japanese Patent Unexamined Publication (JP Kokai) 60-78782, 56-146796, 62-164579, 62-169681, and 62-19485). These methods, however, have little effect of improvement. Or, some methods show improved results to some extent, but such results cannot exhibit readily or last for a long time. In most cases, the obtained performance is still unsatisfactory. In addition, some methods for improvement cannot avoid the side effects of a coloring reaction in the background under the circumstances of high temperature and humidity or a decrease in recording sensitivity. A practical proposal has been thus desired.

As a countermeasure to solve the conventional problems from an utterly different viewpoint from the above, Japanese Patent Unexamined Publication (JP-Kokai) Hei 5-147357 and Hei 5-32601 disclose a method of using as the color developer sulfonylurea compounds instead of conventional organic acidic compounds such as phenols. This proposal to employ the sulfonylurea compounds as the color developer is epoch-making in such a sense that not only novel coloring functional groups are found, but also a thermosensitive recording material can be obtained with remarkably high preservation stability of recorded images. Namely, the thermosensitive recording material can succeed in complete control of de-colorization of recorded images formed in the thermosensitive recording material even when coming into contact with oils and plasticizers, which has been considered to be impossible in the prior art, as well as under various environmental conditions, for example, under the circumstances of high temperature and humidity.

However, by the presence of the above-mentioned sulfonylurea color developer, which can drastically improve the preservation stability of recorded images formed in the thermosensitive recording material, there has been an increasing demand for readily eliminating another drawback of the thermosensitive recording material, that is, the phenomenon that the recorded images become illegible because of the coloring of background to impair the contrast when the recording material is stored under the circumstances of high temperature and humidity. Namely, the proposal to use the sulfonylurea compounds as the color developer disclosed in Japanese Patent Unexamined Publication (JP Kokai) Hei 5-147357 and Hei 5-32601 does not always succeed in preventing the background from coloring under harsher environmental conditions, as currently desired, although the proposal has an effect on the improvement in preservation stability of the recorded images.

The coloring of background at high temperatures is an inevitable consequence of the properties that the thermosensitive recording material causes a coloring reaction by heating. However, owing to the improvement of the color developer and sensitizer it has become possible to reduce the coloring of background to lower levels (Japanese Patent Unexamined Publication (JP Kokai) 63-153183 and Hei 6-1069). Nevertheless, the thermosensitive recording material has been required in recent years to have the performance that recorded images can show such a striking contrast with no coloring of background that they can easily be read even though the environmental conditions become severer, for example, even when the thermosensitive recording type parking tickets and passes are allowed to stand in vehicles under the blazing sun in summer, or when the thermosensitive recording type POS labels attached to the packages of cooked food and packaged lunch boxes sold in supermarkets or convenience stores are heated in the microwave. This marks a turning point of great importance for the thermosensitive recording material.

As a proposal to meet the above-mentioned requirements, there is a method of using compounds with comparatively high molecular weight as the color developer (Japanese Patent Unexamined Publication (JP Kokai) Hei 8-333329). This method, however, is not acceptable for practical use because of low recording sensitivity although the method has a certain effect on the preservation stability of recorded images and the prevention of the background from coloring under the circumstances of high temperature and humidity.

No thermosensitive recording material is proposed that can be provided with both the capability of stability preserving recorded images and the capability of preventing the background from coloring under severer environmental conditions, and also with the fundamental properties satisfactory for a practical use.

The use of compounds having a specific similarity to the compounds of the present invention in structure as the color developer is disclosed in a thermosensitive recording material capable of repeatedly recording images and erasing the same by controlling the heating temperature of the recording material and the cooling speed thereof, which recording material is called a rewritable medium of thermosensitive recording type or a reversible thermosensitive recording material (Japanese Patent Unexamined Publication (JP-Kokai) Hei 7-257033). However, the rewritable thermosensitive recording medium of Japanese Patent Unexamined Publication (JP Kokai) Hei 7-257033 aims at more readily erasing the previously recorded images by the second application of thermal energy, so that it is essential that the color developer comprise a compound having a long-chain aliphatic group. The object and the guideline for designing and selecting the compounds used as the color developer in the above-mentioned application are utterly different from those in the present invention in consideration of one of the major objects of the present invention being to keep images from disappearing after once recorded even by the exposure to high heat.

DISCLOSURE OF THE INVENTION

An object of the present invention is to provide a thermosensitive recording material with high sensitivity, which is free of the above-mentioned shortcomings, and can exhibit high degree of whiteness as a thermosensitive paper, can prevent white background portions from coloring and recorded images from decolorizing in an environmental resistance test, in particular, on the assumption that the recording material is placed under the circumstances of high temperature, for example, in vehicles under the blazing sun in summer or in microwave ovens for cooking by the application of heat, and can exhibit excellent oil resistance and plasticizer resistance of colored images so that long-term preservation stability can be ensured. The present invention provides a thermosensitive recording material that can be used as recording sheets for facsimile machines and word processors, which are required to have high sensitivity and long-term preservation stability, and in addition, as recording sheets for CRT image printers. The present invention provides a thermosensitive recording material that can be used, for example, not only as thermosensitive recording type passes for freeways and toll roads and as passenger tickets, parking tickets and admission tickets issued by automatic ticket vending machines, but also as coupon tickets and commutation tickets required to have preservability, and also as labels for a POS bar code system that is attached to the package side of food packed with a poly(vinyl chloride) film, in other words, the labels inevitably coming into contact with plasticizers and fats and oils.

The present invention includes the following aspects:

[1] A thermosensitive recording material comprising a sheet-shaped support and a thermosensitive recording layer which is formed on at least one surface of the support and comprises a colorless or light-colored dye precursor and a color developer capable of reacting with the dye precursor and inducing color formation therein upon application of heat thereto, the color developer comprising at least one compound selected from the group consisting of compounds represented by the following general formulas (I) to (V):

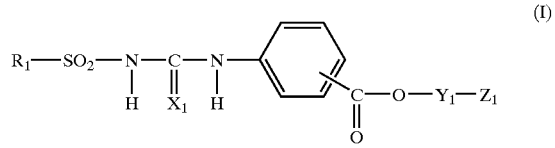

wherein $R_1$ is at least one member selected from the group consisting of a substituted or unsubstituted aromatic hydrocarbon group and a substituted or unsubstituted aliphatic (and alicyclic) hydrocarbon group; $X_1$ is oxygen atom or sulfur atom; $Y_1$ is a bivalent group having 2 or more carbon atoms; $Z_1$ is a monovalent group having at least one hetero atom, provided that $Z_1$ is not a group including sulfonylurea group (—$SO_2NHCONH$—); and benzene ring has at least one $COOY_1Z_1$ group, provided that a plurality of $COOY_1Z_1$ groups may be the same or different when there are two or more, although one $COOY_1Z_1$ group is preferable;

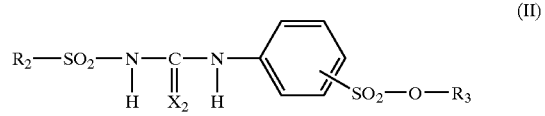

wherein $R_2$ is at least one member selected from the group consisting of a substituted or unsubstituted aromatic hydrocarbon group and a substituted or unsubstituted aliphatic (and alicyclic) hydrocarbon group; $R_3$ is a monovalent organic residue; $X_2$ is oxygen atom or sulfur atom; and benzene ring has at least one —$SO_2OR_3$ group, provided that a plurality of —$SO_2OR_3$ groups may be the same or different when there are two or more, although one —$SO_2OR_3$ group is preferable;

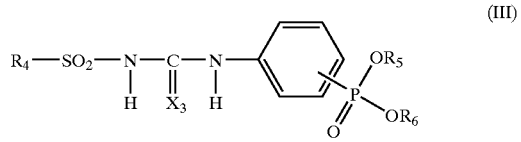

wherein $R_4$ is at least one member selected from the group consisting of a substituted or unsubstituted aromatic hydrocarbon group and a substituted or unsubstituted aliphatic (and alicyclic) hydrocarbon group; $R_5$ and $R_6$ are each independently a monovalent organic residue; $X_3$ is oxygen atom or sulfur atom; and benzene ring has at least one —$PO_3(R_5)(R_6)$ group, provided that a plurality of —$PO_3(R_5)(R_6)$ groups may be the same or different when there are two or more, although one —$PO_3(R_5)(R_6)$ group is preferable;

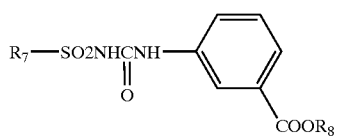

(IV)

wherein $R_7$ is at least one member selected from the group consisting of an unsubstituted aromatic ring group and a substituted aromatic ring group having at least one member selected from the group consisting of methyl group and chlorine atom; $R_8$ is one member selected from the group consisting of an alkyl group, an aralkyl group, an unsubstituted aromatic ring group, and a substituted aromatic ring group; and benzene ring has at least one —$COOR_8$ group, provided that a plurality of —$COOR_8$ groups may be the same or different when there are two or more, although one —$COOR_8$ group is preferable; and

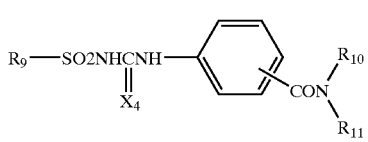

(V)

wherein $X_4$ is oxygen atom or sulfur atom; $R_9$ is a member selected from the group consisting of an unsubstituted aromatic ring group and a substituted aromatic ring group having at least one member selected from the group consisting of an alkyl group, an alkoxyl group, and a halogen atom; $R_{10}$ and $R_{11}$ are each independently a member selected from the group consisting of a hydrogen atom, an alkyl group, an aralkyl group, a group prepared by substituting a part of an alkyl moiety of the aralkyl group with a hetero atom, and a substituted or unsubstituted aromatic ring group; and benzene ring has at least one —$CONR_{10}(R_{11})$ group, provided that a plurality of —$CONR_{10}(R_{11})$ groups may be the same or different when there are two or more, although one —$CONR_{10}(R_{11})$ group is preferable.

[2] The thermosensitive recording material as described in the aspect [1], wherein the compound of general formula (I) is a compound represented by the following general formula (VI):

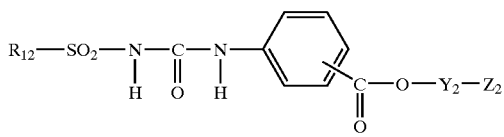

(VI)

wherein $R_{12}$ is an unsubstituted aromatic hydrocarbon group or a substituted aromatic hydrocarbon group having at least one member selected from the group consisting of an alkyl group, an alkoxyl group, and a halogen atom; $Y_2$ is a bivalent group having 2 or more carbon atoms; $Z_2$ is a substituted sulfonyl group having at least one member selected from the group consisting of an alkyl group, an aryl group, and an aralkyl group, or a substituted imido group having at least one member selected from the group consisting of an alkyl group, an aryl group, and an aralkyl group; and benzene ring has at least one —$COOY_2Z_2$ group, provided that a plurality of —$COOY_2Z_2$ groups may be the same or different when there are two or more, although one —$COOY_2Z_2$ group is preferable.

[3] The thermosensitive recording material as described in the aspect [1], wherein the compound of general formula (I) is at least one compound selected from the group consisting of compounds represented by the following general formulas (VII), (VIII) and (IX):

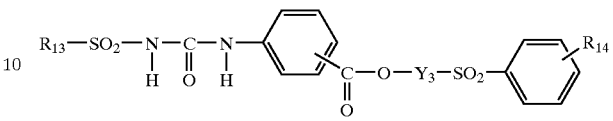

(VII)

wherein $R_{13}$ is an unsubstituted aromatic hydrocarbon group or a substituted aromatic hydrocarbon group having at least one member selected from the group consisting of methyl group, methoxy group, and chlorine atom; $R_{14}$ is a member selected from the group consisting of a hydrogen atom, chlorine atom, a nitro group, an alkyl group, an alkoxyl group, an aryl group, an aryloxy group, an aralkyl group, and an aralkyloxy group, provided that two or more members represented by $R_{14}$ may be independently bonded to a benzene ring as substituents; $Y_3$ is a bivalent group having 2 or more carbon atoms; and the other benzene ring has at least one ester group including $Y_3$, provided that a plurality of ester groups including $Y_3$ may be the same or different when there are two or more, although one ester group including $Y_3$ is preferable;

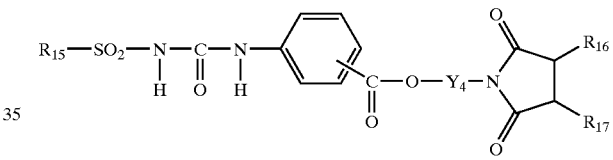

(VIII)

wherein $R_{15}$ is an unsubstituted aromatic hydrocarbon group or a substituted aromatic hydrocarbon group having at least one member selected from the group consisting of methyl group, methoxy group, and chlorine atom; $R_{16}$ and $R_{17}$ are each independently a hydrogen atom, an alkyl group, an aryl group or an aralkyl group, or $R_{16}$ and $R_{17}$ may form cyclopentane ring, cyclohexane ring, dicyclopentane ring or benzene ring in combination; $Y_4$ is a bivalent group having 2 or more carbon atoms; and benzene ring has at least one ester group including $Y_4$, provided that a plurality of ester groups including $Y_4$ may be the same or different when there are two or more, although one ester group including $Y_4$ is preferable; and

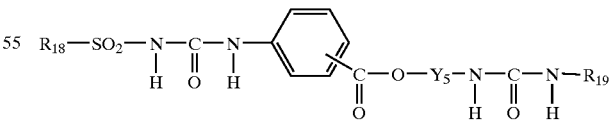

(IX)

wherein $R_{18}$, is an unsubstituted aromatic hydrocarbon group or a substituted aromatic hydrocarbon group having at least one member selected from the group consisting of methyl group, methoxy group, and chlorine atom; $R_{19}$ is a member selected from the group consisting of an alkyl group, an aryl group and an aralkyl group; $Y_5$ is a bivalent group having 2 or more carbon atoms; and benzene ring has at least one ester group including $Y_5$, provided that a plurality of ester groups including $Y_5$ may be the same or different when there are two or more, although one ester group including $Y_5$ is preferable.

[4] The thermosensitive recording material as described in the aspect [1], wherein, in the above-mentioned color developer represented by general formula (V), at least one of $R_{10}$ or $R_{11}$ is a group comprising a straight-chain alkyl group, with the straight-chain alkyl moiety having 8 carbon atoms or less.

[5] The thermosensitive recording material as described in the aspect [1], wherein the above-mentioned color developer represented by general formula (V) is a compound of the following general formula (X) where the —$CONR_{10}(R_{11})$ group is at the m-position:

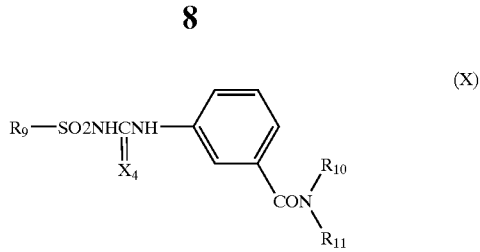

wherein $X_4$, $R_9$, $R_{10}$, and $R_{11}$ are each the same as defined in formula (V).

[6] The thermosensitive recording material as described in the aspects [1], [4] and [5], wherein, in the above-mentioned color developer represented by general formula (V) or (X), $X_4$ is oxygen atom.

[7] 3-p-toluenesulfonylpropyl 4-p-toluenesulfonylaminocarbonylamino benzoate represented by the following chemical formula (XI):

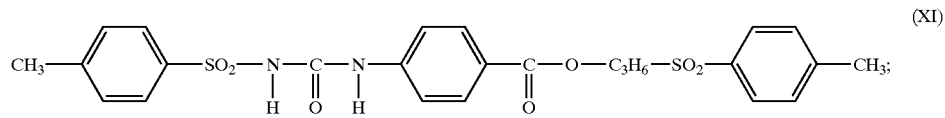

4-[4-(4-iso-propoxyphenylsulfonyl)phenoxy)]butyl 4-p-toluene-sulfonylamino carbonylaminobenzoate represented by the following chemical formula (XII):

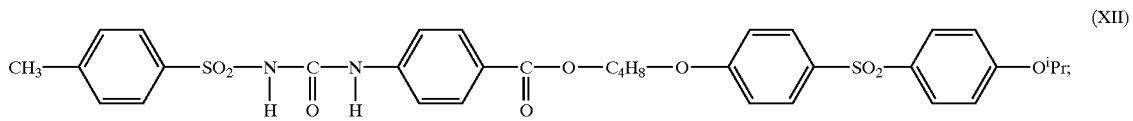

N-3-(3-p-toluenesulfonylaminocarbonylaminobenzoyloxy) propylphthalimide represented by the following chemical formula (XIII):

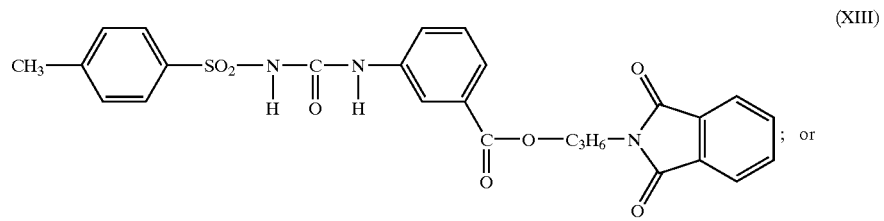

N-phenyl-N 3-(4-p-toluenesulfonylaminocarbonylaminobenzoyloxy) propylurea represented by the following chemical formula (XIV):

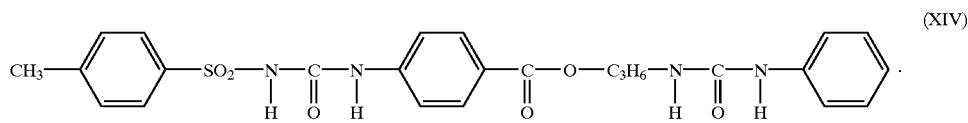

[8] A color developer comprising at least one compound selected from the group consisting of the compounds (XI), (XII) (XIII) and (XIV) described in the aspect [7].

[9] A color developer comprising at least one compound selected from the group consisting of the compounds represented by general formulas (I) to (V) described in the aspect [1].

[10] A thermosensitive recording material comprising the color developer described in the aspect [8].

In the present specification, the imido group may be imino group (OC—NH—C) or acid imide (OC—NH—CO). The acid imide may be a compound prepared by substituting two hydrogen atoms of ammonia with acyl groups, or a cyclic imide derived from acyl group of a dibasic acid. The acid imide is preferable in the present invention.

In the above-mentioned color developer represented by general formula (V), when $R_{10}$ or $R_{11}$ is a substituent comprising a straight-chain alkyl group, it is preferable that the straight-chain alkyl moiety have 8 carbon atoms or less because decolorization of recording at high temperatures can be further reduced. In addition, when the above-mentioned color developer comprises at least one compound selected from the compounds of formula (X) having the substituent at the m-position, there can be obtained a thermosensitive paper with still more improved high-temperature heat resistance.

The compounds represented by chemical formulas (XI), (XII) (XIII) and (XIV) are novel compounds.

BEST MODE FOR CARRYING OUT THE INVENTION

The compounds of general formulas (I) to (V) according to the present invention act as color developers. Namely, the compounds of general formulas (I) to (V) do not have a phenolic hydroxyl group or an acidic functional group such as carboxyl group, but sulfonylurea group in the molecule of the compounds, thereby exhibiting remarkable color development performance with respect to basic leuco dyes. It is considered such excellent properties that a white background portion can be prevented from coloring, in particular, under the circumstances of high temperature, and a recorded image can be prevented from decolorizing be totally supported by the overall characteristics provided by the compounds of the present invention.

As the $R_1$ group in the above-mentioned general formula (I), an aromatic hydrocarbon group having 6 to 20 carbon atoms and an aliphatic hydrocarbon group having 1 to 15 carbon atoms are preferable. Specific examples are phenyl group, 2-naphthyl group, p-tolyl group, o-tolyl group, m-tolyl group, p-chlorophenyl group, p-methoxyphenyl group, benzyl group, cyclohexyl group, methyl group and ethyl group.

The $Y_1$ group in the above-mentioned general formula (I) is not particularly limited as long as it is a bivalent group having 2 or more carbon atoms. Any members constituted by about 30 carbon atoms or less, selected from the group shown below are desirable.

(a) Bivalent groups prepared by removing two hydrogen atoms from chain or cyclic aliphatic hydrocarbon, e.g., ethylene group, trimethylene group, tetramethylene group, pentamethylene group, hexamethylene group, nonamethylene group, 1-methyl-1,3-trimethylene group having a substituent in the side chain thereof, 2,3-dimethyl-1,4-tetramethylene group, 1,4-cyclohexyl group, and 1,4-cyclohexanedimethylene group.

(b) Bivalent groups prepared by removing two hydrogen atoms from a compound in which part of the chain or cyclic aliphatic hydrocarbon is substituted with a hetero atom, or bivalent groups prepared by removing two hydrogen atoms from a compound in which part of the chain or cyclic aliphatic hydrocarbon is substituted with an aromatic compound and a hetero atom, e.g., 1,5-(3-oxapentylene) group, 1,5-(3-thiopentylene) group, 2,5-(1-oxacyclohexylene) group, 1-oxacyclohexane-2,5-dimethylene group, 1,8-(3,6-dioxaoctylene) group, 1,12-(3,6,9-trioxadodecylene) group, 2-phenyleneoxyethylene group, 3-phenyleneoxypropylene group, 4-phenyleneoxybutyl group, and 1,3-bis-phenyleneoxypropylene group.

(c) Bivalent groups prepared by removing two hydrogen atoms from an alkyl group or an alkyl group partially substituted with a hetero atom of an aromatic compound substituted with the alkyl group or the alkyl group partially substituted with a hetero atom, e.g., α,α'-(p-xylylene) group, α,α'-(m-xylylene) group, β, β'-(1,4-di(dimethylene) benzene) group, γ,γ'-(1,4-di(trimethylene)benzene) group, and a bivalent group prepared by removing β,β' hydrogen atoms from p-hydroquinone diethyl ether.

Examples of the $Z_1$ group in the above-mentioned general formula (I) are hydroxyl group, carboxylic acid group, sulfonic acid group, nitro group, cyano group, formyl group, formyl ester group, formyl amide group, halogen atom, amino group having a substituent such as alkyl group, aryl group or aralkyl group, alkoxyl group, carbonyl group, (thio)carboxyl group, oxycarbonyl group, (thio)amide group, aminocarbonyl group, (thio)urea group, sulfonyl group, sulfonyloxy group, oxysulfonyl group, sulfonylamide group, aminosulfonyl group, and phosphoric acid group. A cyclic imido group of which nitrogen atom is bonded to the aforementioned $Y_1$ group is also used as the $Z_1$ group.

Specific examples of the color developer compounds represented by general formula (I) according to the present invention include 2-p-toluenesulfonylethyl 4-p-toluenesulfonylaminocarbonylaminobenzoate, 2-p-toluenesulfonylethyl 3-p-toluenesulfonylaminocarbonylaminobenzoate, 3-p-toluenesulfonylpropyl 4-p-toluenesulfonylaminocarbonylaminobenzoate, 3-p-toluenesulfonylpropyl 3-p-toluenesulfonylaminocarbonylaminobenzoate, 4-p-toluenesulfonylbutyl 4-p-toluenesulfonylaminocarbonylaminobenzoate, 4-p-toluenesulfonylbutyl 3-p-toluenesulfonylaminocarbonylaminobenzoate, 5-p-toluenesulfonyl-3-oxapentyl 4-p-toluenesulfonylaminocarbonylaminobenzoate, 5-p-toluenesulfonyl-3-oxapentyl 3-p-toluenesulfonylaminocarbonylaminobenzoate, 8-p-toluenesulfonyl-3,6-dioxaoctyl 4-p-toluenesulfonylaminocarbonylaminobenzoate, 8-p-toluenesulfonyl-3,6-dioxaoctyl 3-p-toluenesulfonylaminocarbonylaminobenzoate, 12-p-toluenesulfonyl-3,6,9-trioxado-decyl 4-p-toluenesulfonylaminocarbonylaminobenzoate, 12-p-toluenesulfonyl-3,6,9-trioxadodecyl 3-p-toluenesulfonylaminocarbonylaminobenzoate, 9-p-toluenesulfonylnonyl 4-p-toluenesulfonylaminocarbonylaminobenzoate, 9-p-toluenesulfonylnonyl 3-p-toluenesulfonylaminocarbonylaminobenzoate, 4-p-toluenesulfonylmethylcyclohexylmethyl 4-p-toluenesulfonylaminocarbonylaminobenzoate, 4-p-toluenesulfonylmethylcyclohexylmethyl 3-p-toluenesulfonylaminocarbonylaminobenzoate, 4-p- toluenesulfonylmethylphenylmethyl 4-p-toluenesulfonylaminocarbonylaminobenzoate, 4-p-toluenesulfonylmethylphenylmethyl 3-p-toluenesulfonylaminocarbonylaminobenzoate, 3-[4-(4-isopropoxyphenyl sulfonyl)phenoxy)]propyl 4-p-toluenesulfonylaminocarbonylamino-benzoate, 3-[4-(4-isopropoxyphenylsulfonyl)phenoxy)]propyl 3-p-toluenesulfonylamino carbonylaminobenzoate, 4-[4-(4-isopropoxyphenylsulfonyl)phenoxy)]butyl 4-p-toluenesulfonylaminocarbonylaminobenzoate, 4-[4-(4-isopropoxyphenyl sulfonyl)phenoxy)]butyl 3-p-toluenesulfonylaminocarbonylaminobenzoate, 3-p-toluenesulfonylpropyl methylsulfonylaminocarbonylaminobenzoate, 3-p-toiuenesulfonylpropyl ethylsulfonylaminocarbonylaminobenzoate, 3-p-toluenesulfonylpropyl cyclohexylsulfonylaminocarbonylaminobenzoate, 4-p-toluenesulfonylbutyl methylsulfonylaminocarbonylaminobenzoate, 4-p-toluenesulfonylbutyl ethylsulfonylaminocarbonylaminobenzoate, 4-p-toluenesulfonylbutyl cyclohexylsulfonylaminocarbonylaminobenzoate, 5-p-toluenesulfonyl-3-oxapentyl methylsulfonylaminocarbonylaminobenzoate, 5-p-toluenesulfonyl-3-oxapentyl ethylsulfonylaminocarbonylaminobenzoate, 5-p-toluenesulfonyl-3-oxapentyl cyclohexylsulfonylaminocarbonylamino benzoate, 8-p-toluenesulfonyl-3,6-dioxaoctyl methylsulfonylamino-carbonyl aminobenzoate, 8-p-toluenesulfonyl-3,6-dioxaoctyl ethylsulfonylamino carbonylaminobenzoate, 8-p-toluenesulfonyl-3,6-dioxaoctyl cyclohexyl sulfonylaminocarbonylaminobenzoate, 9-p-toluenesulfonylnonyl methylsulfonylaminocarbonylaminobenzoate, 9-p-toluenesulfonylnonyl ethylsulfonylaminocarbonylaminobenzoate, 9-p-toluenesulfonylnonyl cyclohexylsulfonylaminocarbonylaminobenzoate, N-2-(3-p-toluenesulfonylaminocarbonylaminobenzoyloxy) ethylphthalimide, N-2-(4-p-toluenesulfonylaminocarbonylaminobenzoyloxy) ethylphtha-limide, N-3-(3-p-toluenesulfonylaminocarbonylaminobenzoyloxy)propyl-phthalimide, N-3-(4-p-toluenesulfonylaminocarbonylaminobenzoyloxy) propylphthalimide, N-4-(3-p-toluenesulfonylaminocarbonylamino-benzoyloxy) butylphthalimide, N-4-(4-p-toluenesulfonylaminocarbonylaminobenzoyloxy) butylphthalimide, N-2-(3-p-toluenesulfonylaminocarbonylaminobenzoyloxy) ethylsuccinimide, N-2-(4-p-toluenesulfonylaminocarbonylaminobenzoyloxy) ethylsuccinimide, N-3-(3-p-toluenesulfonylaminocarbonylaminobenzoyloxy) propylsuccinimide, N-3-(4-p-toluenesulfonylaminocarbonylaminobenzoyloxy) propylsuccinimide, N-4-(3-p-toluenesulfonylaminocarbonylaminobenzoyloxy) butylsuccinimide, N-4-(4-p-toluenesulfonylaminocarbonylaminobenzoyloxy) butylsuccinimide, N-2-(3-p-toluenesulfonylaminocarbonylaminobenzoyloxy) ethylhexahydro phthalimide, N-2-(4-p-toluenesulfonylaminocarbonylaminobenzoyloxy) ethylhexahydrophthalimide, N-3-(3-p-toluenesulfonylaminocarbonylamino benzoyloxy) propylhexahydrophthalimide, N-3-(4-p-toluenesulfonylamino carbonylaminobenzoyloxy) propylhexahydrophthalimide, N-4-(3-p-toluenesulfonylaminocarbonylaminobenzoyloxy) butylhexahydrophthalimide, N-4-(4-p-toluenesulfonylaminocarbonylaminobenzoyloxy) butylhexahydro phthalimide, N-methyl-N 3-(4-p-toluenesulfonylaminocarbonylamino benzoyloxy)propyl (thio)urea, N-methyl-N 3-(3-p-toluenesulfonylamino carbonylamino-benzoyloxy)propyl(thio)urea, N-methyl-N 4-(4-p-toluenesulfonylaminocarbonylaminobenzoyloxy) butyl(thio)urea, N-methyl-N 4-(3-p-toluenesulfonylaminocarbonylaminobenzoyloxy)butyl(thio) urea, N-ethyl-N 3-(4-p-toluenesulfonylaminocarbonylaminobenzoyloxy)propyl (thio)urea, N-ethyl-N 3-(3-p-toluenesulfonylaminocarbonylaminobenzoyloxy)propyl (thio)urea, N-ethyl-N 4-(4-p-toluenesulfonylaminocarbonylamino benzoyloxy)butyl (thio)urea, N-ethyl-N 4-(3-p-toluenesulfonylaminocarbonylamino-benzoyloxy)butyl (thio)urea, N-propyl-N 3-(4-p-toluenesulfonylaminocarbonylaminobenzoyloxy) propyl (thio)urea, N-propyl-N 3-(3-p-toluenesulfonylaminocarbonylaminobenzoyloxy)propyl (thio)urea, N-propyl-N 4-(4-p-toluenesulfonylaminocarbonylaminobenzoyloxy)butyl(thio) urea, N-propyl -N4-(3-p-toluenesulfonyl-aminocarbonylaminobenzoyloxy)butyl(thio)urea, N-isopropyl-N 3-(4-p-toluenesulfonylaminocarbonylaminobenzoyloxy)propyl (thio)urea, N-isopropyl-N 3-(3-p-toluenesulfonylaminocarbonylamino benzoyloxy)propyl (thio)urea, N-isopropyl-N 4-(4-p-toluene-sulfonylamino carbonylaminobenzoyioxy)butyl(thio)urea, N-iso-propyl-N 4-(3-p-toluenesulfonylaminocarbonylamino-benzoyloxy) butyl(thio)urea, N-butyl-N 3-(4-p-toluenesulfonyl-aminocarbonylaminobenzoyloxy) -(3-p-toluenesulfonylaminocarbonylaminobenzoyloxy)propyl (thio)urea, N-butyl-N 4-(4-p-toluenesulfonylaminocarbonylaminobenzoyloxy)butyl(thio) urea, N-butyl-N 4-(3-p-toluenesulfonylaminocarbonyl-amino benzoyloxy)butyl(thio)urea, N-tert-butyl-N 3-(4-p-toluenesulfonylamino carbonylaminobenzoyloxy)propyl (thio)urea, N-tert-butyl-N 3-(3-p-toluenesulfonylaminocarbonylaminobenzoyloxy)propyl (thio)urea, N-tert-butyl-N 4-(4-p-toluenesulfonylaminocarbonylaminobenzoyloxy)butyl(thio) urea, N-tert-butyl-N 4-(3-p-toluenesulfonylaminocarbonylaminobenzoyloxy)butyl(thio) urea, N-hexyl-N 3-(4-p-toluenesulfonylaminocarbonylamino benzoyloxy)propyl (thio)urea, N-hexyl-N 3-(3-p-toluenesulfonylamino carbonylaminobenzoyloxy)propyl(thio)urea, N-hexyl-N 4-(4-p-toluenesulfonylaminocarbonylaminobenzoyloxy) butyl(thio)urea, N-hexyl-N 4-(3-p-toluenesulfonylaminocarbonylaminobenzo-yloxy)butyl (thio)urea, N-cyclohexyl-N 3-(4-p-toluenesulfonyl-aminocarbonylaminobenzoyloxy)propyl(thio)urea, N-cyclo-hexyl-N 3-(3-p-toluenesulfonylaminocarbonylamino benzoyloxy)propyl (thio)urea, N-cyclohexyl-N 4-(4-p-toluenesulfonylamino carbonylaminobenzoyloxy)butyl(thio)urea, N-cyclohexyl-N 4-(3-p-toluenesulfonylaminocarbonylaminobenzoyloxy)

butyl(thio)urea, N-phenyl-N2-(4-p-toluenesulfonylaminocarbonylaminobenzoyloxy)ethyl(thio)urea, N-phenyl-N 2-(3-p-toluenesulfonylaminocarbonylaminobenzoyloxy)ethyl(thio)urea, N-phenyl-N 3-(4-p-toluenesulfonylaminocarbonylaminobenzoyloxy)propyl(thio)urea, N-phenyl-N 3-(3-p-toluenesulfonylaminocarbony-lamino benzoyloxy)propyl(thio)urea, N-phenyl-N 4-(4-p-toluenesulfonylaminocarbonylaminobenzoyloxy)butyl(thio)urea, N-phenyl-N 4-(3-p-toluenesulfonylaminocarbonylaminobenzoyloxy)butyl(thio)urea, N-p-tolyl-N 3-(4-p-toluenesulfonylaminocarbonylaminobenzoyloxy)propyl(thio)urea, N-p-tolyl-N 3-(3-p-toluenesulfonylaminocarbonylaminobenzoyloxy) propyl(thio)urea, N-p-tolyl-N 4-(4-p-toluenesulfonylaminocarbonylaminobenzoyloxy) butyl(thio)urea, N-p-tolyl-N 4-(3-p-toluenesulfonylaminocarbonylaminobenzoyloxy) butyl(thio) rea, N-p-methoxyphenyl-N 3-(4-p-toluenesulfonylaminocarbonylaminobenzoyloxy) propyl(thio)urea, N-p-methoxyphenyl-N 3-(3-p-toluenesulfonylaminocarbonylaminobenzoyloxy)propyl(thio)urea, N-p-methoxyphenyl-N 4-(4-p-toluenesulfonylaminocarbonylaminobenzoyloxy)butyl(thio)urea, N-p-methoxyphenyl-N 4-(3-p-toluenesulfonylaminocarbonylaminobenzoyloxy)butyl(thio)urea, 1,2-di-3-toluenesulfonylpropyl 4-(N-p-toluenesulfonylaminocarbonylamino) phthalate, and 1,3-di-3-toluenesulfonylpropyl 5-(N-p-toluenesulfonylaminocarbonylamino) isophthalate. In the above, (thio)urea means urea or thiourea.

As the aforementioned compound of general formula (I), the compound represented by general formula (VI) is preferable, and the compounds represented by general formulas (VII), (VIII) and (IX) are more preferable.

As for the $R_2$ group in the above-mentioned general formula (II), an aromatic hydrocarbon group having 6 to 20 carbon atoms and an aliphatic hydrocarbon group having 1 to 15 carbon atoms are preferable. Specific examples of such groups are phenyl group, 2-naphthyl group, p-tolyl group, o-tolyl group, m-tolyl group, p-chlorophenyl group, p-methoxyphenyl group, benzyl group, cyclohexyl group, methyl group, and ethyl group. The $R_3$ group is not particularly limited as long as it is a monovalent organic residue. In particular, an alkyl group having 8 carbon atoms or less, an aralkyl group substituted with an alkyl group having 8 carbon atoms or less, and an aryl group are desirable.

Specific examples of the color developer compounds represented by general formula (II) according to the present invention include methyl 4-p-toluenesulfonylaminocarbonylaminobenzenesulfonate, ethyl 4-p-toluenesulfonylaminocarbonylaminobenzenesulfonate, propyl 4-p-toluenesulfonylaminocarbonylaminobenzenesulfonate, isopropyl 4-p-toluenesulfonylaminocarbonylaminobenzenesulfonate, butyl 4-p-toluenesulfonylaminocarbonylaminobenzenesulfonate, isobutyl 4-p-toluenesulfonylaminocarbonylaminobenzenesulfonate, tert-butyl 4-p-toluenesulfonylaminocarbonylaminobenzenesulfonate, cyclohexyl 4-p-toluenesulfonylaminocarbonylaminobenzenesulfonate, phenyl 4-p-toluenesulfonylaminocarbonylaminobenzenesulfonate, o-tolyl 4-p-toluenesulfonylaminocarbonylaminobenzenesulfonate, p-tolyl 4-p-toluenesulfonylaminocarbonylaminobenzenesulfonate, m-tolyl 4-p-toluenesulfonylaminocarbonylaminobenzenesulfonate, methyl 3-p-toluenesulfonylaminocarbonylaminobenzenesulfonate, ethyl 3-p-toluenesulfonylaminocarbonylaminobenzenesulfonate, propyl 3-p-toluenesulfonylaminocarbonylaminobenzenesulfonate, isopropyl 3-p-toluenesulfonylaminocarbonylaminobenzenesulfonate, butyl 3-p-toluenesulfonylaminocarbonylaminobenzenesulfonate, isobutyl 3-p-toluenesulfonylaminocarbonylaminobenzenesulfonate, tert-butyl 3-p-toluenesulfonylaminocarbonylaminobenzenesulfonate, cyclohexyl 3-p-toluenesulfonylaminocarbonylaminobenzenesulfonate, phenyl 3-p-toluenesulfonylaminocarbonylaminobenzenesulfonate, o-tolyl 3-p-toluenesulfonylaminocarbonylaminobenzenesulfonate, p-tolyl 3-p-toluenesulfonylaminocarbonylaminobenzenesulfonate, m-tolyl 3-p-toluenesulfonylaminocarbonylaminobenzenesulfonate, methyl cyclohexylsulfonylaminocarbonylaminobenzenesulfonate, ethyl cyclohexylsulfonylaminocarbonylaminobenzenesulfonate, propyl cyclohexylsulfonylaminocarbonylaminobenzenesulfonate, isopropyl cyclohexylsulfonylaminocarbonylaminobenzenesulfonate, butyl cyclohexylsulfonylaminocarbonylaminobenzenesulfonate, isobutyl methylsulfonylaminocarbonylaminobenzenesulfonate, tert-butyl ethylsulfonylaminocarbonylaminobenzenesulfonate, cyclohexylmethylsulfonylaminocarbonylaminobenzenesulfonate, phenyl ethylsulfonylaminocarbonylaminobenzenesulfonate, o-tolyl cyclo-hexylsulfonylaminocarbonylaminobenzenesulfonate, p-tolyl methylsulfonylaminocarbonylaminobenzenesulfonate, m-tolyl ethylsulfonylaminocarbonylaminobenzenesulfonate, dimethyl 4-p-toluenesulfonylaminocarbonylaminobenzene-1,2-disulfonate, and dimethyl 5-p-toluenesulfonylaminocarbonylaminobenzene-1,3-disulfonate.

As for the $R_4$ group in the above-mentioned general formula (III), an aromatic hydrocarbon group having 6 to 20 carbon atoms and an aliphatic hydrocarbon group having 1 to 15 carbon atoms are preferable. Specific examples of such groups are phenyl group, 2-naphthyl group, p-tolyl group, o-tolyl group, m-tolyl group, p-chlorophenyl group, p-methoxyphenyl group, benzyl group, cyclohexyl group, methyl group, and ethyl group. The $R_5$ group and $R_6$ group are not particularly limited as long as each group is a monovalent organic residue. In particular, an alkyl group having 8 carbon atoms or less, an aralkyl group substituted with an alkyl group having 8 carbon atoms or less, and an aryl group are desirable.

Specific examples of the color developer compounds represented by general formula (III) according to the present invention include dimethyl 4-p-toluenesulfonyl-aminocarbonylaminobenzenephosphonate, diethyl 4-p-toluenesulfony-laminocarbonylaminobenzenephosphonate, dipropyl 4-p-toluenesulfonylaminocarbonylaminobenzenephosphonate, diisopropyl 4-p-toluenesulfonylaminocarbonylaminobenzenephosphonate, dibutyl 4-p-toluenesulfonylaminocarbonylaminobenzenephosphonate, diisobutyl 4-p-toluenesulfonylaminocarbonylaminobenzenephosphonate, di-tert-butyl 4-p-toluenesulfonylaminocarbonylaminobenzenephosphonate, dicyclohexyl 4-p-toluenesulfonylaminocarbonylaminobenzenephosphonate, diphenyl 4-p-toluenesulfonylaminocarbonylaminobenzenephosphonate, di-o-tolyl 4-p-toluenesulfonylaminocarbonylaminobenzenephosphonate, di-p-tolyl 4-p-toluenesulfonylaminocarbonylaminobenzenephosphonate, di-m-tolyl 4-p-toluenesulfonylaminocarbonylaminobenzenephosphonate, dimethyl 3-p-toluenesulfonylaminocarbonylaminobenzenephosphonate, diethyl 3-p-toluenesulfonylaminocarbonylaminobenzenephosphonate, dipropyl 3-p-toluenesulfonylaminocarbonylaminobenzenephosphonate, diisopropyl 3-p-toluenesulfonylaminocarbonylaminobenzenephosphonate, dibutyl 3-p-toluenesulfonylaminocarbonylaminobenzenephosphonate, diisobutyl 3-p-toluenesulfonylaminocarbonylaminobenzenephosphonate, di-tert-butyl 3-p-toluenesulfonylaminocarbonylaminobenzenephosphonate, dicyclohexyl 3-p-toluenesulfonylaminocarbonylaminobenzenephosphonate, diphenyl 3-p-toluenesulfonylaminocarbonylaminobenzenephosphonate, di-o-tolyl 3-p-toluenesulfonylaminocarbonylaminobenzenephosphonate, di-p-tolyl 3-p-toluenesulfonylaminocarbonylaminobenzenephosphonate, di-m-tolyl 3-p-toluenesulfonylaminocarbonylaminobenzenephosphonate, dimethyl cyclohexylsulfonylaminocarbony-laminobenzenephosphonate, diethyl cyclohexylsulfonylaminocarbonylaminobenzenephosphonate, dipropyl cyclohexylsulfonylaminocarbonylaminobenzenephosphonate, diisopropyl cyclohexylsulfonylaminocarbonylaminobenzenephosphonate, dibutyl cyclohexylsulfonylaminocarbonylaminobenzenephosphonate, diisobutyl methylsulfonylaminocarbonylaminobenzenephosphonate, di-tert-butylethylsulfonylaminocarbonylaminobenzenephosphonate, dicyclohexyl methylsulfonylaminocarbonylaminobenzenephosphonate, diphenyl ethylsulfonylaminocarbonylaminobenzenephosphonate, di-o-tolyl methylsulfonylaminocarbonylaminobenzenephosphonate, di-p-tolyl ethylsulfonylaminocarbonylaminobenzenephosphonate, di-m-tolyl cyclohexylsulfonylaminocarbonylaminobenzenephosphonate, tetramethyl 4-p-toluenesulfonylaminocarbonylaminobenzene-1,2-diphosphonate, and tetramethyl 5-p-toluenesulfonylaminocarbonylaminobenzene-1,3-diphosphonate.

Specific examples of the $R_7$ group in the aforementioned general formula (IV) are unsubstituted aromatic ring groups such as phenyl group and 2-naphthyl group, and aromatic ring groups substituted with one member selected from the group consisting of methyl group and chlorine atom, such as p-tolyl group, o-tolyl group, m-tolyl group, and p-chlorophenyl group.

The $R_8$ group in the aforementioned general formula (IV) is one member selected from the group consisting of an alkyl group, an aralkyl group, and an unsubstituted and substituted aromatic ring group. Examples of the alkyl group are propyl group, isopropyl group, butyl group, isobutyl group, hexyl group, cyclohexyl group, octyl group, dodecyl group, and octadecyl group. The alkyl group having 18 carbon atoms or less is preferable. When the number of carbon atoms exceeds 18, there is a risk that the decolorization phenomenon will take place in printed portions.

Generally, specific examples of the aralkyl group are hydrocarbon-substituted groups such as benzyl group, phenetyl group, 2-naphthylmethyl group, and 2-naphthylethyl group. According to the definition of the present invention, the aralkyl group further includes phenoxyethyl group, 2-naphthoxyethyl group and the like, that is, the groups obtained by substituting a part of an alkyl moiety by oxygen atom. Examples of the unsubstituted and substituted aromatic ring groups are p-tolyl group and p-chlorophenyl group.

Examples of the compounds of formula (IV) include methyl 3-(p-toluenesulfonylaminocarbonylamino)benzoate, methyl 3-(m-toluenesulfonylaminocarbonylamino)benzoate, methyl 3-(o-toluenesulfonylaminocarbonylamino)benzoate, methyl 3-(benzenesulfonylaminocarbonylamino)benzoate, ethyl 3-(p-toluenesulfonylaminocarbonylamino)benzoate, ethyl 3-(m-toluenesulfonylaminocarbonylamino)benzoate, ethyl 3-(o-toluenesulfonylaminocarbonylamino)benzoate, ethyl 3-(benzenesulfonylaminocarbonylamino)benzoate, propyl 3-(p-toluenesulfonylaminocarbonylamino)benzoate, propyl 3-(m-toluenesulfonylaminocarbonylamino)benzoate, propyl 3-(o-toluenesulfonylaminocarbonylamino)benzoate, propyl 3-(benzenesulfonylaminocarbonylamino)benzoate, propyl 3-(p-chlorobenzenesulfonylamino carbonylamino)benzoate, propyl 3-(m-chlorobenzenesulfonylaminocarbonynlamino)benzoate, butyl 3-(p-toluenesulfonylaminocarbonynlamino)benzoate, butyl 3-(o-toluenesulfonylaminocarbonylamino)benzoate, butyl 3-(m-toluenesulfonylaminocarbonylamino)benzoate, benzyl 3-(p-toluenesulfonylaminocarbonylamino)benzoate, benzyl 3-(m-toluenesulfonylaminocarbonylamino)benzoate, cyclohexyl 3-(p-toluenesulfonylaminocarbonylamino)benzoate, butyl 3-(p-chlorobenzenesulfonylaminocarbonylamino)benzoate, butyl 3-(o-chlorobenzenesulfonylaminocarbonylamino)benzoate, octyl 3-(p-toluenesulfonylaminocarbonylamino)benzoate, octyl 3-(m-toluenesulfonylaminocarbonylamino)benzoate, octyl 3-(o-toluenesulfonylaminocarbonylamino)

benzoate, octyl 3-(benzenesulfonylaminocarbonylamino)benzoate, dodecyl 3-(p-toluenesulfonylaminocarbonylamino)benzoate, dodecyl 3-(m-toluenesulfonylaminocarbonylamino)benzoate, dodecyl 3-(o-toluenesulfonylaminocarbonylamino)benzoate, dodecyl 3-(benzenesulfonylaminocarbonylamino)benzoate, octadecyl 3-(p-toluenesulfonylaminocarbonylamino)benzoate, octadecyl 3-(m-toluenesulfonylaminocarbonylamino)benzoate, octadecyl 3-(o-toluenesulfonylaminocarbonylamino)benzoate, octadecyl 3-(benzenesulfonylaminocarbonylamino)benzoate, phenyl3-(m-toluenesulfonylaminocarbonylamino)benzoate, tolyl 3-(p-toluenesulfonylcarbonylamino)benzoate, and chlorophenyl 3-(p-toluenesulfonylaminocarbonylamino)benzoate.

Examples of m-position substituted compounds among those represented by the above-mentioned general formula (V) include compounds represented by the above-mentioned general formula (X) wherein $X_4$, $R_9$, $R_{10}$ and $R_{11}$ are the same as those in the formula (V).

Specific examples of the groups represented by $R_9$ in the above-mentioned general formulas (V) and (X) are phenyl group, 2-naphthyl group, p-tolyl group, o-tolyl group, m-tolyl group, and p-chlorophenyl group.

The $R_{10}$ and $R_{11}$ in the above general formula (V) are each independently one member selected from the group consisting of a hydrogen atom, an alkyl group, an aralkyl group, and an unsubstituted and substituted aromatic ring group.

Specific examples of the alkyl group are propyl group, isopropyl group, butyl group, isobutyl group, hexyl group, cyclohexyl group, and octyl group. When the alkyl group is a straight-chain alkyl group, there is a tendency that the preservability of printed portions formed in the thermosensitive paper is especially preferable under the circumstances of high temperature by choosing the above-mentioned substituent with 8 or less carbon atoms.

Generally, specific examples of the aralkyl group are hydrocarbon-substituted groups such as benzyl group, phenetyl group, 2-naphthylmethyl group, and 2-naphthylethyl group. The aralkyl group further includes phenoxyethyl group, 2-naphthoxyethyl group, phenylthioethyl group and the like, that is, the groups obtained by substituting a part of an alkyl moiety of the aralkyl group by a hetero atom.

Examples of the unsubstituted and substituted aromatic ring groups are p-tolyl group and p-chlorophenyl group.

Examples of the compounds of general formulas (V) and (X) include N-methyl 3-(p-toluenesulfonylaminocarbonylamino)benzamide, N-methyl 3-(m-toluenesulfonylaminocarbonylamino)benzamide, N-methyl 3-(o-toluenesulfonylaminocarbonylamino)benzamide, N-methyl 3-(benzenesulfonylaminocarbonylamino)benzamide, N-ethyl 3-(p-toluenesulfonylaminocarbonylamino)benzamide, N-ethyl 3-(m-toluenesulfonylaminocarbonylamino)benzamide, N-ethyl 3-(o-toluenesulfonylaminocarbonylamino)benzamide, N-ethyl 3-(benzenesulfonylaminocarbonylamino)benzamide, N-propyl 2-(p-toluenesulfonylaminocarbonylamino)benzamide, N-propyl 2-(m-toluenesulfonylaminocarbonylamino)benzamide, N-propyl 2-(o-toluenesulfonylaminocarbonylamino)benzamide, N-propyl 2-(benzenesulfonylaminocarbonylamino)benzamide, N-propyl 2-(p-chlorobenzenesulfonylaminocarbonylamino)benzamide, N-propyl 2-(m-chlorobenzenesulfonylaminocarbonylamino)benzamide, N-propyl 3-(p-toluenesulfonylaminocarbonylamino)benzamide, N-propyl 3-(m-toluenesulfonylaminocarbonylamino)benzamide, N-propyl 3-(o-toluenesulfonylaminocarbonylamino)benzamide, N-propyl 3-(benzenesulfonylaminocarbonylamino)benzamide, N-propyl 3-(p-chlorobenzenesulfonylaminocarbonylamino)benzamide, N-propyl 3-(m-chlorobenzenesulfonylaminocarbonylamino)benzamide, N-propyl 4-(p-toluenesulfonylaminocarbonylamino)benzamide, N-propyl 4-(m-toluenesulfonylaminocarbonylamino)benzamide, N-propyl 4-(o-toluenesulfonylaminocarbonylamino)benzamide, N-propyl 4-(benzenesulfonylaminocarbonylamino)benzamide, N-propyl 4-(p-chlorobenzenesulfonylaminocarbonylamino)benzamide, N-propyl 4-(m-chlorobenzenesulfonylaminocarbonylamnino)benzamide, N-butyl 3-(p-toluenesulfonylaminocarbonylamino)benzamide, N-butyl 3-(o-toluenesulfonylaminocarbonylamino)benzamide, N-butyl 3-(m-toluenesulfonylaminocarbonylamino)benzamide, N-butyl 4-(p-toluenesulfonylaminocarbonylamino)benzamide, N-butyl 4-(o-toluenesulfonylaminocarbonylamino)benzamide, N-butyl 4-(m-toluenesulfonylaminocarbonylamino)benzamide, N-benzyl 3-(p-toluenesulfonylaminocarbonylamino)benzamide, N-benzyl 3-(m-toluenesulfonylaminocarbonylamino)benzamide, N-butyl 3-(p-toluenesulfonylaminocarbonylamino)benzamide, N-butyl 3-(p-chlorobenzenesulfonylaminocarbonylamino)benzamide, N-butyl 3-(o-chlorobenzenesulfonylaminocarbonylamino)benzamide, N-octyl 3-(p-toluenesulfonylaminocarbonylamino)benzamide, N-octyl 3-(m-toluenesulfonylaminocarbonylamino)benzamide, N-octyl 3-(benzenesulfonylaminocarbonylamino)benzamide, N-cyclododecyl 3-(p-toluenesulfonylaminocarbonylamino)benzamide, N-cyclododecyl 3-(m-toluenesulfonylaminocarbonylamino)benzamide, N,N-dioctyl 3-(p-toluenesulfonylaminocarbonylamino)benzamide, N,N-dioctyl 3-(m-toluenesulfonylaminocarbonylamino)benzamide, N-n-propyl 3-(p-toluenesulfonylaminothiocarbonylamino)benzamide, N-n-butyl 3-(p-toluenesulfonylaminothiocarbonylamino)benzamide, N-n-octyl 3-(p-toluenesulfonylaminothiocarbonylamino)benzamide, N-cyclododecyl 3-(p-toluenesulfonylaminothiocarbonylamino)benzamide, N-n-propyl 4-(p-toluenesulfonylaminothiocarbonylamino)benzamide, and N-n-octyl 4-(p-toluenesulfonylaminothiocarbonylamino)benzamide.

Of these compounds, compounds of general formula (V), which have a straight-chain hydrocarbon group with 8 or less carbon atoms and which are in the form of a meta-compound as represented by general formula (X) are particularly preferable because when a thermosensitive paper is produced using such compounds, the recognition of printed portions becomes better under the circumstances of high temperature. Namely, white background portions causes no coloring, thereby increasing the contrast between the background portions and printed portions. Further, it is preferable that $X_4$ be oxygen atom in general formulas (V) and (X).

The compounds represented by the above-mentioned general formulas may be used alone or in combination.

The aforementioned compounds of general formulas (I) to (V) can be synthesized in accordance with the methods described in Examples.

Among these compounds which are remarkably excellent color developers are 3-p-toluenesulfonylpropyl 4-p-toluenesulfonylamino carbonylaminobenzoate represented by the above-mentioned chemical formula (XI), 4-[4-(4-isopropoxyphenylsulfonyl)phenoxy)]butyl 4-p-toluenesulfonylaminocarbonylaminobenzoate represented by the above-mentioned chemical formula (XII), N-3-(3-p-toluenesulfonylaminocarbonylaminobenzoyloxy) propylphthalimide represented by the above-mentioned chemical formula (XIII), and N-phenyl-N 3-(4-p-toluenesulfonylaminocarbonylaminobenzoyloxy) propylurea represented by the above-mentioned formula (XIV) in terms of plasticizer resistance and heat resistance.

Leuco dyes such as triphenylmethane compounds, fluoran compounds, and diphenylmethane compounds are used as the dye precursors in the present invention. At least one compound may be selected from the conventional leuco compounds, for example, 3-(4-diethylamino-2-ethoxyphenyl)-3-(1-ethyl-2-methylindol-3-yl)-4-azaphthalide, crystal violet lactone, 3-(N-ethyl-N-isopentylamino)-6-methyl-7-anilinofluoran, 3-diethylamino-6-methyl-7-anilinofluoran, 3-diethylamino-6-methyl-7-(o,p-dimethylanilino)fluoran, 3-(N-ethyl-N-p-toluidino)-6-methyl-7-anilino fluoran, 3-pyrrolidino-6-methyl-7-anilinofluoran, 3-dibutylamino-6-methyl-7-anilinofluoran, 3-(N, N-dipentylamino)-6-methyl-7-anilinofluoran, 3-(N-cyclohexyl-N-methylamino)-6-methyl-7-anilinofluoran, 3-diethylamino-7-(o-chloroanilino) fluoran, 3-diethylamino-7-(o-chloroanilino) fluoran, 3-dibutylamino-7-(m-trifluoromethylanilino)fluoran, 3-diethylamino-6-methyl-7-chlorofluoran, 3-diethylamino-6-methylfluoran, 3-cyclohexylamino-6-chlorofluoran, and 3-(N-ethyl-N-hexylamino)-6-methyl-7-(p-chloroanilino) fluoran.

In the present invention, as long as the desired effects are not hindered, the conventional color developers such as phenols, color developer compounds having one or two sulfonylurea groups in one molecule, or organic acids can be used in combination with the compounds selected from the compounds of general formulas (I) to (V) according to the present invention.

Examples of such conventional color developers are 2,2-bis (4-hydroxyphenyl)propane (bisphenol A), 1,1-bis (4-hydroxyphenyl)-1-phenylethane, 1,4-bis (1-methyl-1-(4-hydroxyphenyl)ethyl)benzene, 1,3-bis (1-methyl-1-(4-hydroxyphenyl)ethyl)benzene, dihydroxydiphenylether (Japanese Patent Unexamined Publication (JP Kokai) Hei 1-180382), benzyl p-hydroxybenzoate (Japanese Patent Unexamined Publication (JP Kokai) 52-140483), bisphenol S, 4-hydroxy-4 isopropyloxydiphenylsulfone (Japanese Patent Unexamined Publication (JP Kokai) 60-13852), 1,1-di(4-hydroxyphenyl)cyclohexane, 1,7-di(4-hydroxyphenylthio)-3,5-dioxaheptane (Japanese Patent Unexamined Publication (JP Kokai) 59-52694), 3,3 diallyl-4,4-dihydroxydiphenylsulfone (Japanese Patent Unexamined Publication (JP Kokai) 60-208286), and 2,4-bis (phenylsulfonyl) phenol (Japanese Patent Unexamined Publication (JP Kokai) Hei 8-269000).

In addition, the compounds having one sulfonylurea group in one molecule, such as N-(p-toluenesulfonyl)-N phenylurea, N-(p-toluenesulfonyl)-N (p-methoxyphenyl) urea, N-(p-toluenesulfonyl)-N(o-tolyl)urea, N-(p-toluenesulfonyl)-N(m-tolyl)urea, N-(p-toluenesulfonyl)-N (p-tolyl)urea, N-(p-toluenesulfonyl)-N(o-chlorophenyl) urea, N-(benzenesulfonyl)-N-phenylurea, and N-(p-chlorobenzenesulfonyl)-N-phenylurea, which are disclosed in Japanese Patent Unexamined Publication (JP Kokai) Hei 5-32601 can be used as the color developers other than the phenols.

Further, there can be employed the compounds having two or more sulfonylurea groups in one molecule, which are generally called high-preservation type color developers, e.g., 4,4-bis(p-toluenesulfonylamino carbonylamino) diphenylmethane and 1,8-(3,6-dioxaoctylene)bis (4-(p-toluenesulfonylaminocarbonylamino)benzoate as disclosed in Japanese Patent Unexamined Publication (JP-Kokai) Hei 5-147357; color developer compounds having a phenolic structure and sulfone group in one molecule, such as 2,4-bis(phenylsulfonyl)phenol, as described in Japanese Patent Unexamined Publication (JP Kokai) Hei 8-269000; and color developer compounds having two p-hydroxydiphenylsulfone structures in one molecule, those structures being bonded with ethylene, ethylene oxide or polyethylene oxide chain, as disclosed in Japanese Patent Unexamined Publication (JP Kokai) Hei 8-333329, for example, the following compound of formula (XV):

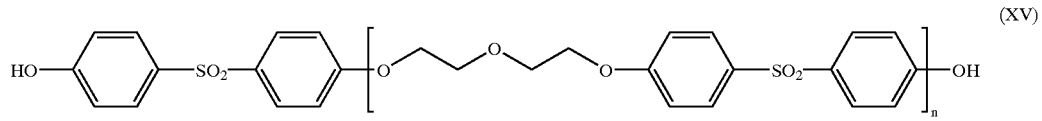

(XV)

In the above, n is an integer of 1 or more, and there is no particular upper limit on number. For example, n may be about 1000.

Of the compounds represented by the above-mentioned formula (XV), a mixture of a compound where n is 1, that is, 1,7-(1,4,7-trioxyheptene) bis (4-(p-hydroxyphenylsulfonyl)benzene) and a compound where n is 2, that is, 4,4 bis(7-(4-(p-hydroxyphenylsulfonyl) phenyl)-1,4,7-trioxyhept-1-yl)diphenylsulfone is preferable.

In addition, there can be employed color developers having such a chemical structure that a phenolic structure is present in one molecule and the molecular weight is 1000 or more, that is, a compound having the following chemical formula (XVI), more specifically, a compound described in Nippon Kagakukai, 76th Spring Convention Proceedings I 2PB152, pp. 618 (1999). The addition of this compound further improves the plasticizer resistance and oil resistance.

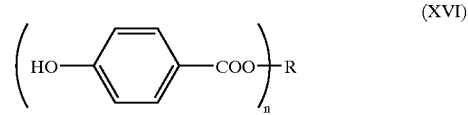

(XVI)

$n \geq 2$
R:oligomer residue

Furthermore, in the present invention, conventional thermofusible materials (sensitizers) may be used together so as not to impair the desired effects. Representative examples of such materials are phenyl 1-hydroxy-2-naphthoate, (Japanese Patent Unexamined Publication (JP Kokai) 57-191089), p-benzylbiphenyl (Japanese Patent Unexamined Publication (JP Kokai) 60-82382), benzyl naphthyl ether (Japanese Patent Unexamined Publication (JP Kokai) 58-87094), dibenzyl terephthalate (Japanese Patent Unexamined Publication (JP Kokai) 58-98285), benzyl p-benzyloxybenzoate (Japanese Patent Unexamined Publication (JP Kokai) 57-201691), diphenyl carbonate, ditolyl carbonate (Japanese Patent Unexamined Publication (JP Kokai) 58-136489), m-terphenyl (Japanese Patent Unexamined Publication (JP Kokai) 57-89994), 1,2-bis(m-tolyloxy) ethane (Japanese Patent Unexamined Publication (JP Kokai) 60-56588), 1,5-bis(p-methoxyphenoxy)-3-oxapentane (Japanese Patent Unexamined Publication (JP Kokai) 62-181183), oxalic acid diesters (Japanese Patent Unexamined Publication (JP Kokai) 64-1583), and 1,4-bis (p-tolyloxy)benzene (Japanese Patent Unexamined Publication (JP Kokai) Hei 2-153783).

The thermosensitive coloring layer of the thermosensitive recording material according to the present invention may further comprise waxes, and in addition, preferably organic or inorganic pigments. The thermosensitive recording layer further comprises a binder to fix the above-mentioned components to the support.

Generally, it is preferable that the content of the aforementioned leuco dye in the thermosensitive coloring layer be in the range of 5 to 20 mass % (weight %) of the mass (weight) on a dry basis of the thermosensitive recording layer. It is preferable that the content of the color developer according to the present invention be in the range of 5 to 50 mass % with respect to the thermosensitive recording layer. When the sensitizer is added, the content of the sensitizer is preferably in the range of 5 mass % to 50 mass %, more preferably in the range of 10 mass % to 40 mass %.

In the case where the thermosensitive recording layer comprises the conventional phenolic color developer or organic acid color developer, the content of such a color developers is preferably in the range of 5 to 40 mass %. When the waxes and the white pigment are contained in the thermosensitive recording layer, the content of the waxes and that of the white pigment are preferably in the range of 2 mass % to 20 mass %, and in the range of 2 mass % to 50 mass %, respectively. The content of the binder is generally in the range of 5 mass % to 20 mass %.

As for the above-mentioned organic or inorganic pigments, there can be employed inorganic finely-divided particles of calcium carbonate, silica, zinc oxide, titanium oxide, aluminum hydroxide, zinc hydroxide, barium sulfate, clay, calcined clay, talc, and surface treated calcium carbonate and silica; and organic finely-divided particles of urea-formalin resin, styrene/methacrylic acid copolymer, and polystyrene resin.

Further, paraffin, amide waxes, bisimide waxes, and metallic salts of higher fatty acids, which are conventionally known, can be used as the waxes.

Examples of the aforementioned binders include water-soluble polymers such as polyvinyl alcohol with various molecular weights, starch and derivatives thereof, cellulose derivatives such as methoxy cellulose, carboxymethyl cellulose, methyl cellulose, and ethyl cellulose, sodium polyacrylate, polyvinyl pyrrolidone, acrylic amide/acrylic ester copolymer, acrylic amide/acrylic ester/methacrylic acid terpolymer, alkali salts of styrene/maleic anhydride copolymer, polyacrylamide, sodium alginate, gelatin, and casein; and a variety of latexes such as polyvinyl acetate, polyurethane, styrene/butadiene copolymer, polyacrylic acid, polyacrylate, vinyl chloride/vinyl acetate copolymer, polybutyl methacrylate, ethylene/vinyl acetate copolymer, and styrene/butadiene/acryl copolymer.

For the sheet-shaped support for use in the thermosensitive recording material of the present invention, any material may be selected from paper (including acid paper and neutral paper), coated paper surface-coated with a pigment or latex, laminated paper, synthetic paper made of polyolefin resins, and plastic film. A thermosensitive recording material is produced by applying a coating liquid comprising a mixture of the required components as mentioned above to at least one surface of a sheet-shaped support and drying the coating liquid. It is preferable that the coating amount be in the range of 1 to 15 g/m², more preferably 2 to 10 g/m² on a dry basis of the coating liquid layer.

The thermosensitive recording material of the present invention may further comprise overcoat layers such as a protective layer and a printing layer which are provided on the thermosensitive coloring layer.

In addition, undercoat layers comprising a pigment (preferably, oil-absorption pigment) and an adhesive may be provided between the support and the above-mentioned thermosensitive recording layer.

The thermosensitive recording material of the present invention shows not only high recording sensitivity and whiteness (high brightness), but also excellent long-term preservation stability of recording, that is, excellent environmental resistance such as heat resistance and moisture resistance, and oil resistance and plasticizer resistance of recorded images, also less coloring of background and almost no decolorization of recorded images under the circumstances of high temperature and humidity, in particular, when exposed to severe environmental conditions equivalent to the case where the recording material is placed in vehicles under the blazing sun in summer, or subjected to heat application cooking using the microwave oven in a kithen. There can be thus provided a thermosensitive recording material that can be advantageously used as image recording paper, paper for cash dispenser, passenger tickets, passes, parking tickets, admission tickets, commutation tickets, labels such as POS labels, and cards such as pre-paid cards.

EXAMPLES

The present invention will now be explained more specifically by referring to Examples shown below.

The terms arts(s) and mean art(s)by mass (weight) and ass (weight) % respectively unless otherwise noted.

Synthesis Example 1

Synthesis of 3-p-toluene-sulfonylpropyl 4-p-toluenesulfonylamino-carbonylaminobenzoate (Chemical formula (XI)):

(1) Synthesis of intermediate, i.e., 3-p-toluenesulfonylpropyl 4-aminobenzoate.

In a three-necked flask equipped with a thermometer, a reflux condenser and a dropping funnel 6.0 g of sodium toluenesulfinate and 80 ml of ethanol were placed. With stirring the mixture by a magnetic stirrer, 16.0 g of 3-bromo-1-chloropropane was added to the mixture at room temperature. After the resultant reaction suspension was stirred at room temperature, the suspension was refluxed at 100° C. for 5 hours and thereafter cooled to room temperature. The reaction suspension was added to 800 ml of hexane, and the resultant mixture was vigorously stirred, so that a white solid separated out as a precipitate. The white solid was filtered off, washed with water, and purified by recrystallization, whereby 5.9 g of white crystals, 3-chloropropyl p-tolyl sulfone, was obtained. Next, 3.0 g of p-aminobenzoic acid was added to 120 ml of N,N-dimethylacetamide to prepare a solution, and 1.8 g of potassium carbonate (anhydrous) was added to the solution. With stirring the resultant mixture by a magnetic stirrer, 5.0 g of the white crystals obtained by the previous step was added to the mixture at room temperature. After the resultant reaction suspension was stirred at room temperature, the mixture was refluxed at 130° C. for 5 hours and thereafter cooled to room temperature. The reaction suspension was poured into 800 ml of water and vigorously stirred, whereby a white solid separated out. The white solid was separated by filtration and purified by recrystallization, so that 6.2 g of a product was obtained as white crystals.

The analytical values of the above-mentioned white crystals are as follows:

Melting point; 75° C.

Results of NMR (in $CDCl_3$)(unit: ppm):

δ1.92 (m, 2H), 2.40 (s, 3H), 3.40 (t, 2H), 4.14 (t, 2H), 6.53 (d, 2H), 7.45 (d, 2H), 7.59 (d, 2H), 7.83 (d, 2H).

In addition, a peak which is considered to be due to NH appeared around δ5.97 (s, 2H).

Results of IR measurement (by KBr tablet method) (only characteristic absorptions):

1693 $cm^{-1}$ (due to carbonyl group of ester group)

1343, 1157 $cm^{-1}$ (due to sulfonyl group)

3117 $cm^{-1}$ (due to amino group)

(2) Synthesis of 3-p-toluenesulfonylpropyl 4-p-toluenesulfonylaminocarbonyl aminobenzoate (Chemical formula (XI))

In a three-necked flask equipped with a dropping funnel, a thermometer and a reflux condenser 6.2 g of 3-p-toluenesulfonylpropyl 4-aminobenzoate was placed and stirred with the addition thereto of 200 ml of toluene to dissolve 3-p-toluenesulfonylpropyl 4-aminobenzoate therein. With stirring the mixture solution by a magnetic stirrer, 4.2 g of p-toluenesulfonylisocyanate was added dropwise to the mixture through the dropping funnel at room temperature. A large amount of white solid precipitated after continuous stirring of the reaction mixture. The resultant reaction mixture was heated to 70° C. for 2 hours, and then cooled and filtered off. Thus, 10.2 g of a product was obtained as white crystals.

The analytical values of the above-mentioned white crystals are as follows:

Melting point; 158° C.

Results of NMR (in $(CD_3)_2SO$)(unit: ppm):

δ1.92 (m, 2H), 2.36 (s, 3H), 2.39 (s, 3H), 3.42 (t, 2H), 4.22 (t, 2H), 7.35 (d, 2H), 7.42 (d, 2H), 7.45 (d, 2H), 7.69 (d, 2H), 7.78 (d, 2H), 7.86 (d, 2H).

In addition, peaks which are considered to be due to NH appeared around δ3.33 (s, 1H) and 9.23 (s, 1H).

Results of IR measurement (by KBr tablet method)(only characteristic absorptions):

1723 $cm^{-1}$ (due to carbonyl group of urea group)

1689 $cm^{-1}$ (due to carbonyl group of ester group)

1343, 1157 $cm^{-1}$ (due to sulfonyl group).

Synthesis Example 2

4-[4-(4-iso-propoxyphenyl-sulfonyl)phenoxy]butyl 4-p-toluenesulfonylamino-carbonylaminobenzoate (Chemical formula (XII)):

9.1 g of 4-[4-(4-iso-propoxyphenylsulfonyl)phenoxy)] butyl 4-p-toluenesulfonylaminocarbonylaminobenzoate (white crystals) was synthesized in the same manner as in Synthesis Example 1. In synthesis of the raw material, i.e., 4-[4-(4-iso-propoxyphenylsulfonyl)phenoxy]butyl 4-aminobenzoate (6.8 g), 3-chloro-propyl p-tolyl sulfone used as the starting material of the esterification in Synthesis Example 1 was replaced by 4-bromo-4-(4-iso-propoxyphenylsulfonyl)phenoxybutyl (8.0 g), and p-aminobenzoic acid (2.6 g) was used as a material for esterification.

The analytical values of the obtained white crystals after the final reaction with p-toluene sulfonyl isocyanate are as follows:

Melting point; 133° C.

Results of NMR (in $(CD_3)_2SO$)(unit: ppm):

δ1.26 (d, 6H), 1.82 (m, 4H), 2.41 (s, 3H), 4.07 (m, 2H), 4.19 (m, 2H), 4.26 (m, 1H), 7.35 (d, 2H), 7.42 (d, 2H), 7.15 (m, 4H), 7.43 (m, 4H), 7.84 (m, 8H)

In addition, peaks which are considered to be due to NH appeared around δ3.33 (s, 1H) and 9.23 (s, 1H).

Results of IR measurement (by KBr tablet method)(only characteristic absorptions):

1721 $cm^{-1}$ (due to carbonyl group of urea group)

1688 $cm^{-1}$ (due to carbonyl group of ester group)

1345, 1156 $cm^{-1}$ (due to sulfonyl group).

Synthesis Example 3

N-3-(3-p-toluenesulfonylaminocarbonylaminobenzoyloxy) propylphthalimide (Chemical formula (XIII)):

10.2 g of N-3-(3-p-toluenesulfonylaminocarbonylaminobenzoyloxy) ropy-lphthalimide (white crystals) was synthesized in the same manner as in Synthesis Example 1 except that 3-chloropropyl p-tolyl sulfone was replaced by N-3-bromopropylphthalimide (13.7 g) as the material for esterification, and that p-aminobenzoic acid was replaced by m-aminobenzoic acid (7.0 g).

The analytical values of the white crystals thus obtained after the final reaction with p-toluene sulfonyl isocyanate are as follows:

Melting point; 190° C.

Results of NMR (in $(CD_3)_2SO$) (unit: ppm):

δ2.06 (m, 2H), 2.38 (s, 3H), 3.73 (t, 2H), 4.25 (t, 2H), 7.29 (m, 1H), 7.42 (m, 2H), 7.52 (m, 1H), 7.75 (m, 2H), 7.81 (m, 2H).

In addition, peaks which are considered to be due to NH appeared around δ3.32 (s, 1H) and 9.02 (s, 1H).

Results of IR measurement (by KBr tablet method)(only characteristic absorptions):

1725 $cm^{-1}$ (due to carbonyl group of urea group)

1692 $cm^{-1}$ (due to carbonyl group of ester group)

1343, 1158 $cm^{-1}$ (due to sulfonyl group)

Synthesis Example 4

Synthesis of N-phenyl-N 3-(4-p-toluenesulfonylaminocarbonylaminobenzoyloxy) propylurea (Chemical formula (XIV)):

(1) Synthesis of intermediate, i.e., N-3-p-nitrophenylpropyl-N phenylurea.

In a three-necked flask equipped with a thermometer, a reflux condenser and a dropping funnel 3.0 g of 3-amino- 1-propanol and 80 ml of tetrahydrofuran were placed. With stirring the mixture by a magnetic stirrer, 20 ml of tetrahydrofuran dissolving 5.9 g of phenyl isocyanate therein was added to the mixture through the dropping funnel at room temperature. The reaction instantaneously proceeded on addition of phenyl isocyanate, and a white product precipitated. To complete the reaction, the reaction mixture was further stirred for 2 hours. The white solid was separated by filtration, washed with water, and purified by recrystallization, whereby 8.1 g of white crystals was obtained. Next, 5.0 g of the white crystals obtained by the previous step and 120 ml of tetrahydrofuran were placed in a three-necked flask equipped with a thermometer, a reflux condenser and a dropping funnel, and 2.8 g of triethylamine was added to the mixture. With stirring the mixture by a magnetic stirrer, 20 ml of tetrahydrofuran dissolving 4.8 g of p-nitrobenzoyl chloride therein was added to the mixture through the dropping funnel. The reaction readily proceeded on addition of the tetrahydrofuran solution of p-nitrobenzoyl chloride, and triethylamine hydrochloride separated out and precipitated. The reaction mixture was further stirred for 4 hours at room temperature in order to complete the reaction. The resultant reaction liquid was added to 800 ml of water and the resultant mixture was vigorously stirred, whereby the triethylamine hydrochloride was dissolved, and in return, a desired product precipitated as a white solid. The white solid was separated by filtration and purified by recrystallization, so that 7.4 g of a product was obtained as white crystals.

The analytical values of the above-mentioned white crystals are as follows:

Melting point; 135° C.

Results of NMR (in CDCl$_3$)(unit: ppm):

δ1.91 (m, 2H), 3.25 (m, 2H), 4.37 (t, 2H), 6.84 (t, 1H), 7.18 (d, 2H), 7.34 (d, 2H), 7.83 (d, 2H), 8.30 (d, 2H).

In addition, peaks which are considered to be due to NH appeared around δ6.24 (m, 1H) and 8.43 (s, 2H).

Results of IR measurement (by KBr tablet method)(only characteristic absorptions):

1688 cm$^{-1}$ (due to carbonyl group of ester group)

1735 cm$^{-1}$ (due to carbonyl group of urea group)

3122 cm$^{-1}$ (due to amino group of urea group)

(2) Synthesis of N-phenyl-N 3-(4-p-toluenesulfonylaminocarbonylaminobenzoyloxy) propylurea (Chemical formula (XIV))

To 7.0 g of N-3-p-nitrophenylpropyl-N phenylurea placed in an autoclave was added 80 ml of tetrahydrofuran and 3.5 g of 5 wt %-Pd/C. After the atmosphere in the autoclave was replaced by hydrogen, the internal pressure was controlled to 2 atmospheric pressure and reduction of nitro group was carried out over a period of 2 hours with stirring. By removing the Pd/C from the mixture by filtration and distilling away the solvent, 6.2 g of a white solid was obtained. Next, in a three-necked flask equipped with a dropping funnel, a thermometer and a reflux condenser 6.2 g of the white solid obtained by the previous step was placed and 200 ml of toluene was added thereto. With stirring the mixture by a magnetic stirrer, 4.0 g of p-toluenesulfonylisocyanate was added dropwise to the above mixture through the dropping funnel at room temperature. A large amount of white solid precipitated after continuous stirring of the reaction mixture. The resultant reaction mixture was refluxed at 120° C. for 2 hours, and then cooled and filtered off. Thus, 10.0 g of a product was obtained as white crystals.

The analytical values of the above-mentioned white crystals are as follows:

Melting point; 158° C.

Results of NMR (in (CD$_3$)$_2$SO)(unit: ppm):

δ1.85 (m, 2H), 2.39 (s, 3H), 3.22 (m, 2H), 4.26 (t, 2H), 6.86 (m, 1H), 7.19 (m, 2H), 7.35 (d, 2H), 7.42 (d, 2H), 7.45 (d, 2H), 7.86 (m, 4H).

In addition, peaks which are considered to be due to NH appeared around δ3.33 (s, 1H), 6.22 (m, 1H), 8.42 (s, 1H), and 9.22 (s, 1H).

Results of IR measurement (by KBr tablet method)(only characteristic absorptions):

1719, 1723 cm$^{-1}$ (due to carbonyl group of urea group)

1687 cm$^{-1}$ (due to carbonyl group of ester group)

1343, 1157 cm$^{-1}$ (due to sulfonyl group).

Synthesis Example 5

Synthesis of butyl 4-p-toluenesulfonylamino carbonylaminobenzenesulfonate:

(1) Synthesis of intermediate, i.e., butyl aminobenzenesulfonate.

In a three-necked flask equipped with a thermometer, a reflux condenser and a dropping funnel 3.4 g of p-sulfonylamide and 120 ml of N,N-diaminoacetamide were placed and 2.8 g of potassium carbonate (anhydrous) was added to the above prepared solution. With stirring the mixture by a magnetic stirrer, 2.7 g of 1-bromobutane was added to the mixture at room temperature. The resultant reaction suspension was cooled to room temperature and poured into 800 ml of water. A white solid precipitated by vigorous stirring. The white solid was separated by filtration and purified by recrystallization, whereby 4.1 g of a product was obtained as white crystals.

The product in the form of white crystals was identified as a desired compound by various instrumental analysis.

(2) Synthesis of butyl 4-p-toluenesulfonylaminocarbonylaminobenzoate.

In a three-necked flask equipped with a dropping funnel, a thermometer and a reflux condenser 3.4 g of butyl aminobenzenesulfonate was placed and 200 ml of toluene was added thereto with stirring to dissolve butyl aminobenzenesulfonate therein. With stirring the resultant mixture by a magnetic stirrer, 3.4 g of p-toluenesulfonylisocyanate was added dropwise to the mixture through the dropping funnel at room temperature. A large amount of white solid precipitated after continuous stirring of the reaction mixture. The reaction mixture was heated to 70° C. for 2 hours and thereafter cooled and filtered off, whereby 5.8 g of a product was obtained as white crystals.

The product in the form of white crystals was identified as a desired compound by various instrumental analysis.

Synthesis Example 6

Synthesis of butyl 3-(p-toluenesul-fonylamino carbonylamino)benzoate:

(1) Synthesis of raw material, i.e., n-butyl 3-aminobenzoate.

In a three-necked flask equipped with a thermometer, a reflux condenser and a dropping funnel 15.6 g of 3-aminobenzoic acid and 120 ml of N,N-dimethylformamide were placed and 16 g of potassium carbonate (anhydrous) was added to the above prepared solution. With stirring the mixture by a magnetic stirrer, 16.3 g of 1-bromobutane was added to the mixture at room temperature. After the resultant reaction suspension was stirred at room temperature, the suspension was refluxed at 130° C. for 5 hours and cooled to room temperature. The reaction suspension was poured into 300 ml of water and vigorously stirred. The aqueous solution thus obtained was extracted from 150 ml of ethyl acetate, and thereafter ethyl acetate was distilled away, whereby 19.6 g of a product was obtained as an oily material.

The oily product was identified as a desired compound by various instrumental analysis.

(2) Synthesis of butyl 3-(p-toluenesulfonylaminocarbonylamino)benzoate.

In a three-necked flask equipped with a dropping funnel, a thermometer and a reflux condenser 15.4 g of n-butyl 3-aminobenzoate was placed and 150 ml of toluene was added thereto with stirring to dissolve n-butyl 3-aminobenzoate therein. With stirring the resultant mixture by a magnetic stirrer, 17.3 g of p-toluenesulfonylisocyanate was added dropwise to the mixture through the dropping funnel at room temperature. Continuous stirring of the reaction mixture caused an exothermic reaction, thereby precipitating a large amount of white solid.

The reaction mixture was heated to 100° C. for 3 hours and thereafter cooled and filtered off, whereby 25.3 g of a product was obtained as white crystals.

The analytical values of the product in the form of white crystals are as follows:

Melting point; 140–143° C.

Results of NMR (in $CDCl_3$)(unit: ppm):

$\delta$=0.98 (t, 3H), 1.48 (m, 2H), 1.76 (m, 2H), 2.43 (s, 3H), 4.33 (t, 2H), 7.34 (d, 2H), 7.42 (t, 1H), 7.79 (m, 2H), 7.86 (d, 2H), 7.94 (s, 1H).

In addition, peaks which are considered to be due to NH appeared around $\delta$=8.16 and 8.55.

Synthesis Example 7

Synthesis of propyl 3-(p-toluenesulfonylaminocarbonylamino)benzoate:

(1) Synthesis of raw material, i.e., n-propyl 3-aminobenzoate.

The procedure in Synthesis Example 6 (1) was repeated except that 16.3 g of 1-bromobutane was replaced by 17.2 g of 1-bromopropane. Thus, 18.4 g of a product was obtained as an oily material.

The oily product was identified as a desired compound by various instrumental analysis.

(2) Synthesis of propyl 3-(p-toluenesulfonylaminocarbonylamino)benzoate.

The procedure in Synthesis Example 6 (2) was repeated except that 15.6 g of n-butyl 3-aminobenzoate was replaced by 14.8 g of n-propyl 3-aminobenzoate. Thus, 24.3 g of a product was obtained as white crystals.

The analytical values of the product in the form of white crystals are as follows:

Melting point; 132–135° C.

Results of NMR (in $CDCl_3$)(unit: ppm):

$\delta$=1.03 (t, 3H), 1.79 (m, 2H), 2.43 (s, 3H), 4.30 (t, 2H), 7.34 (d, 2H), 7.40 (t, 1H), 7.76 (d, 2H), 7.81 (d, 1H), 7.96 (s, 1H).

In addition, a peak which is considered to be due to N—H appeared around $\delta$=8.03.

Synthesis Example 8

Synthesis of methyl 3-(p-toluenesulfonylamino carbonylamino)benzoate.

The procedure in Synthesis Example 6 (2) was repeated except that 15.4 g of n-butyl 3-aminobenzoate was replaced by 16.8 g of n-methyl 3-aminobenzoate. Thus, 23.1 g of a product was obtained as white crystals.

The analytical values of the product in the form of white crystals are as follows:

Melting point; 178–180° C.

Results of NMR (in $CDCl_3$)(unit: ppm):

$\delta$=2.43 (s, 3H), 3.93 (s, 3H), 7.26 (d, 2H), 7.41 (t, 1H), 7.74 (d, 1H), 7.81 (d, 1H), 7.83 (d, 2H), 7.97 (s, 1H).

In addition, peaks which are considered to be due to N—H appeared around $\delta$=8.22 and 8.57.

Synthesis Example 9

Synthesis of ethyl 3-(p-toluenesulfonylamino carbonylamino)benzoate.

The procedure in Synthesis Example 6 (2) was repeated except that 15.4 g of n-butyl 3-aminobenzoate was replaced by 16.3 g of n-ethyl 3-aminobenzoate. Thus, 22.5 g of a product was obtained as white crystals.

The analytical values of the product in the form of white crystals are as follows:

Melting point; 183–185° C.

Results of NMR (in $CDCl_3$)(unit: ppm):

$\delta$=1.40 (t, 3H), 2.43 (s, 3H), 4.40 (q, 2H), 7.33 (d, 2H), 7.40 (t, 1H), 7.75 (d, 1H), 7.77 (d, 1H), 7.83 (d, 2H), 7.95 (t, 1H).

In addition, peaks which are considered to be due to N—H appeared around $\delta$=8.17 and 8.57.

Synthesis Example 10

Synthesis of octyl 3-(p-toluenesulfonylamino carbonylamino)benzoate.

(1) Synthesis of raw material, i.e., n-octyl 3-aminobenzoate.

The procedure in Synthesis Example 6 (1) was repeated except that 16.3 g of 1-bromobutane was replaced by 17.8 g of 1-bromooctyl. Thus, 22.8 g of a product was obtained as an oily material.

The oily product was identified as a desired compound by various instrumental analysis.

(2) Synthesis of octyl 3-(p-toluenesulfonylaminocarbonylamino)benzoate.

The procedure in Synthesis Example 6 (2) was repeated except that 15.4 g of n-butyl 3-aminobenzoate was replaced by 18.1 g of n-octyl 3-aminobenzoate. Thus, 23.8 g of a product was obtained as white crystals.

The analytical values of the product in the form of white crystals are as follows:

Melting point; 111–113° C.

Results of NMR (in $CDCl_3$) (unit: ppm):

$\delta$=0.88 (t, 3H), 1.27–1.45 (m, 10H), 1.77 (m, 2H), 2.43 (s, 3H), 4.33 (m, 2H), 7.33 (d, 2H), 7.41 (t, 1H), 7.78 (d, 1H), 7.78 (d, 1H), 7.84 (d, 2H), 7.95 (s, 1H)

In addition, a peak which is considered to be due to N—H appeared around δ=8.59.

Synthesis Example 11

Synthesis of dodecyl 3-(p-toluenesulfonylaminocarbonylamino)benzoate.

(1) Synthesis of raw material, i.e., n-dodecyl 3-aminobenzoate.

The procedure in Synthesis Example 6 (1) was repeated except that 16.3 g of 1-bromobutane was replaced by 18.7 g of 1-bromododecyl. Thus, 23.5 g of a product was obtained as white crystals.

The product in the form of white crystals was identified as a desired compound by various instrumental analysis.

(2) Synthesis of dodecyl 3-(p-toluenesulfonylaminocarbonylamino)benzoate.

The procedure in Synthesis Example 6 (2) was repeated except that 15.4 g of n-butyl 3-aminobenzoate was replaced by 15.8 g of n-dodecyl 3-aminobenzoate. Thus, 21.6 g of a product was obtained as white crystals.

The analytical values of the product in the form of white crystals are as follows:

Melting point; 110–112° C.

Results of NMR (in $CDCl_3$)(unit: ppm):

δ=0.88 (t, 3H), 1.26–1.40 (m, 10H), 2.43 (s, 3H) 4.33 (m, 2H), 7.33 (d, 2H), 7.40 (t, 1H), 7.75 (d, 1H), 7.77 (d, 1H), 7.85 (d, 2H), 7.95 (s, 1H).

In addition, a peak which is considered to be due to N—H appeared around δ=8.58.

Synthesis Example 12

Synthesis of octadecyl 3-(p-toluenesulfonylaminocarbonylamino)benzoate.

(1) Synthesis of raw material, i.e., n-octadecyl 3-aminobenzoate.

The procedure in Synthesis Example 6 (1) was repeated except that 16.3 g of 1-bromobutane was replaced by 18.7 g of 1-bromooctadecyl. Thus, 23.5 g of a product was obtained as white crystals.

The product in the form of white crystals was identified as a desired compound by various instrumental analysis.

(2) Synthesis of octadecyl 3-(p-toluenesulfonylaminocarbonylamino)benzoate.

The procedure in Synthesis Example 6 (2) was repeated except that 15.4 g of n-butyl 3-aminobenzoate was replaced by 14.7 g of n-octadecyl 3-aminobenzoate. Thus, 20.3 g of a product was obtained as white crystals.

The analytical values of the product in the form of white crystals are as follows:

Melting point; 96° C.

Results of NMR (in $CDCl_3$)(unit: ppm):

δ=0.88 (t, 3H), 1.28–1.46 (m, 30H), 1.77 (m, 2H), 2.43 (s, 3H), 4.32 (t, 2H), 7.35 (d, 2H), 7.40 (t, 1H), 7.77 (d, 2H), 7.81 (d, 2H), 7.94 (s, 1H).

In addition, a peak which is considered to be due to N—H appeared around δ=8.58.

Synthesis Example 13

Synthesis of N-n-propyl 3-(p-toluenesulfonylaminocarbonylamino)benzamide.

(1) Synthesis of raw material, i.e., N-n-propyl 3-nitrobenzamide.

In a round bottom flask 3.0 g of n-propylamine and 100 ml of tetrahydrofuran were placed to prepare a solution, and 4.8 g of pyridine was added thereto. With stirring the resultant mixture by a magnetic stirrer, 9.0 g of 3-nitrobenzoyl chloride was added to the mixture at room temperature. The resultant reaction suspension was stirred at room temperature for 3 days, and thereafter poured into 150 ml of water with vigorous stirring. After the aqueous solution thus prepared was extracted from 50 ml of ethyl acetate, ethyl acetate was distilled away, so that 7.8 g of a product was obtained as a brown solid material.

The analytical values of the brown solid product are as follows:

Results of NMR (in c $CDCl_3$)(unit: ppm):

δ=1.01 (t, 3H), 1.68 (m, 2H), 3.46 (m, 2H), 7.64 (t, 1H), 8.16 (d, 1H), 8.35 (d, 1H), 8.58 (s, 1H).

In addition, a peak which is considered to be due to N—H appeared around δ=6.45.

(2) Synthesis of N-n-propyl 3-aminobenzamide.

In a 200-ml glass vessel 7.7 g of N-n-propyl 3-nitrobenzamide and 2.3 g of a palladium on carbon catalyst were placed, and 80 ml of tetrahydrofuran was gradually added to dissolve N-n-propyl 3-nitrobenzamide therein. The resultant solution was stirred at room temperature for 2 hours in an atmosphere of saturated hydrogen under 2 atmospheric pressure. Thereafter, the palladium on carbon catalyst was removed from the mixture and tetrahydrofuran was distilled away, whereby 6.5 g of a product was obtained as a brown liquid.

The analytical values of the oily product are as follows:

Results of NMR (in $CDCl_3$)(unit: ppm):

δ=0.98 (t, 3H), 1.62 (m, 2H), 3.39 (m, 2H), 6.78 (d, 1H), 7.03 (d, 1H), 7.13 (s, 1H), 7.18 (t, 1H).

In addition, peaks which are considered to be due to N—H appeared around δ3.74 and 6.15.

(3) Synthesis of N-n-propyl 3-(p-toluenesulfonylaminocarbonylamino)benzamide.

In a three-necked flask equipped with a dropping funnel, a thermometer and a reflux condenser 5.8 g of N-n-propyl 3-aminobenzamide was placed and 100 ml of acetonitrile was added with stirring in order to dissolve N-n-propyl 3-aminobenzamide therein. With stirring the mixture by a magnetic stirrer, 7.1 g of p-toluenesulfonylisocyanate was added dropwise to the mixture through the dropping funnel at room temperature. Continuous stirring of the reaction mixture caused an exothermic reaction, thereby precipitating a large amount of white solid.

The reaction mixture was stirred for 2 hours at room temperature and filtered off, whereby 10.5 g of a product was obtained as white crystals.

The analytical values of the product in the form of white crystals are as follows:

Melting point: 162–164° C.

Results of NMR (in $(CD_3)_2SO$)(unit: ppm):

δ=0.87 (t, 3H), 1.50 (m, 2H), 2.40 (s, 3H), 3.18 (m, 2H), 7.32 (t, 1H), 7.45 (t, 4H), 7.78 (s, 1H), 7.85 (d, 2H).

In addition, peaks which are considered to be due to N—H appeared around δ=8.40, 8.92 and 10.77.

Synthesis Example 14

Synthesis of N-n-butyl 3-(p-toluenesulfonylamino carbonylamino)benzamide.

(1) Synthesis of raw material, i.e., N-n-butyl 3-nitrobenzamide.

The procedure in Synthesis Example 13 (1) was repeated except that 3.0 g of n-propylamine was replaced by 3.7 g of n-butylamine. Thus, 9.0 g of a product was obtained as yellow crystals.

The analytical values of the product in the form of yellow crystals are as follows:

Results of NMR (in CDCl$_3$)(unit: ppm):

δ=0.97 (t, 3H), 1.43 (m, 2H), 1.64 (m, 2H), 3.49 (m, 2H), 7.64 (t, 1H), 8.16 (d, 1H), 8.34 (d, 1H), 8.58 (s, 1H).

In addition, a peak which is considered to be due to N—H appeared around δ=6.44.

(2) Synthesis of N-n-butyl 3-aminobenzamide.

The procedure in Synthesis Example 13 (2) was repeated except that 7.7 g of N-n-propyl 3-nitrobenzamide was replaced by 8.2 g of N-n-butyl 3-nitrobenzamide. Thus, 7.1 g of a product was obtained as white crystals.

The analytical values of the product in the form of white crystals are as follows:

Results of NMR (in (CD$_3$)$_2$SO)(unit: ppm): 0

δ=0.89 (t, 3H), 1.30 (m, 2H), 1.47 (m, 2H), 3.20 (m, 2H), 6.67 (d, 1H), 6.92 (d, 1H), 7.00 (s, 1H), 7.05 (t, 1H).

In addition, peaks which are considered to be due to N—H ppeared around δ=5.17 and 8.16.

(3) Synthesis of N-n-butyl 3-(p-toluenesulfonylaminocarbonylamino)benzamide.

The procedure in Synthesis Example 13 (3) was repeated except that 5.8 g of N-n-propyl 3-aminobenzamide was replaced by 6.3 g of N-n-butyl 3-aminobenzamide. Thus, 11.5 g of a product was obtained as white crystals.

The analytical values of the product in the form of white crystals are as follows:

Melting point: 125–128° C.

Results of NMR (in (CD$_3$)$_2$SO)(unit: ppm):

δ=0.89 (t, 3H), 1.30 (m, 2H), 1.47 (m, 2H), 2.40 (s, 3H) 3.19 (m, 2H), 7.32 (t, 1H), 7.45 (t, 4H) 7.77 (s, 1H), 7.85 (d, 2H).

In addition, peaks which are considered to be due to N—H appeared around δ=8.38, 8.94 and 10.77.

Synthesis Example 15

Synthesis of N-n-octyl 3-(p-toluenesulfonylamino carbonylamino)benzamide.

(1) Synthesis of raw material, i.e., N-n-octyl 3-nitrobenzamide.

The procedure in Synthesis Example 13 (1) was repeated except that 3.0 g of n-propylamine was replaced by 6.6 g of n-octylamine. Thus, 11.4 g of a product was obtained in the form of white crystals.

The analytical values of the product as white crystals are as follows:

Results of NMR (in CDCl$_3$)(unit: ppm):

δ=0.88 (t, 3H), 1.28–1.39 (m, 10H), 1.64 (m, 2H), 3.48 (m, 2H), 7.65 (t, 1H), 8.15 (d, 1H), 8.34 (d, 1H), 8.57 (s, 1H).

In addition, a peak which is considered to be due to N—H appeared around δ=6.32.

(2) Synthesis of N-n-octyl 3-aminobenzamide.

The procedure in Synthesis Example 13 (2) was repeated except that 7.7 g of N-n-propyl 3-nitrobenzamide was replaced by 10.3 g of N-n-octyl 3-nitrobenzamide. Thus, 9.0 g of a product was obtained as white crystals.

The analytical values of the product in the form of white crystals are as follows:

Results of NMR (in CDCl$_3$)(unit: ppm):

δ=0.88 (t, 3H), 1.27–1.33 (m, 10H), 1.59 (m, 2H), 3.41 (m, 2H), 6.78 (d, 1H), 7.03 (d, 1H), 7.13 (s, 1H), 7.18 (t, 1H).

In addition, peaks which are considered to be due to N—H appeared around δ=3.79 and 6.10.

(3) Synthesis of N-n-octyl 3-(p-toluenesulfonylaminocarbonylamino)benzamide.

The procedure in Synthesis Example 13 (3) was repeated except that 5.8 g of N-n-propyl 3-aminobenzamide was replaced by 8.1 g of N-n-octyl 3-aminobenzamide. Thus, 11.9 g of a product was obtained as white crystals.

The analytical values of the product in the form of white crystals are as follows:

Melting point: 90–100° C.

Results of NMR (in (CD$_3$)$_2$SO)(unit: ppm):

δ=0.85 (t, 3H), 1.25–1.30 (m, 10H), 1.47 (m, 2H), 2.40 (s, 3H), 3.20 (m, 2H), 7.31 (t, 1H), 7.44 (t, 4H), 7.77 (s, 1H), 7.85 (d, 2H).

In addition, peaks which are considered to be due to N—H appeared around δ=8.38, 8.93 and 10.78.

Synthesis Example 16

Synthesis of N-cyclododecyl 3-(p-toluenesulfonyl aminocarbonylamino)benzamide.

(1) Synthesis of raw material, i.e., N-cyclododecyl 3-nitrobenzamide.

The procedure in Synthesis Example 13 (1) was repeated except that 3.0 g of n-propylamine was replaced by 9.3 g of cyclododecylamine. Thus, 9.7 g of a product was obtained as white crystals.

The product in the form of white crystals was identified as a desired compound by various instrumental analysis.

(2) Synthesis of N-cyclododecyl 3-aminobenzamide.

The procedure in Synthesis Example 13 (2) was repeated except that 7.7 g of N-n-propyl 3-nitrobenzamide was replaced by 12.3 g of N-cyclododecyl 3-nitrobenzamide. Thus, 11.4 g of a product was obtained as white crystals.

The product in the form of white crystals was identified as a desired compound by various instrumental analysis.

(3) Synthesis of N-cyclododecyl 3-(p-toluenesulfonylaminocarbonylamino)benzamide.

The procedure in Synthesis Example 13 (3) was repeated except that 5.8 g of N-n-propyl 3-aminobenzamide was replaced by 9.8 g of N-cyclododecyl 3-aminobenzamide. Thus, 13.9 g of a product was obtained as white crystals.

The analytical values of the product in the form of white crystals are as follows:

Melting point: 125–128° C.

Results of NMR (in (CD$_3$)$_2$SO)(unit: ppm):

δ=1.31–1.65 (m, 22H), 2.40 (s, 3H), 4.11 (m, 1H), 7.31 (t, 1H), 7.44 (t, 4H), 7.74 (s, 1H), 7.85 (d, 2H).

In addition, peaks which are considered to be due to N—H appeared around δ=8.07, 8.91 and 10.75.

Synthesis Example 17

Synthesis of N-n-propyl 4-(p-toluenesulfonylamino carbonylamino)benzamide.

(1) Synthesis of raw material, i.e., N-n-propyl 4-nitrobenzamide.

The procedure in Synthesis Example 13 (1) was repeated except that 3-nitrobenzoyl chloride was replaced by 4-nitrobenzoyl chloride. Thus, 7.9 g of a product was obtained as white crystals.

The product in the form of white crystals was identified as a desired compound by various instrumental analysis.

(2) Synthesis of N-n-propyl 4-aminobenzamide.

The procedure in Synthesis Example 13 (2) was repeated except that N-n-propyl 3-nitrobenzamide was replaced by N-n-propyl 4-nitrobenzamide. Thus, 6.5 g of a product was obtained as a brown liquid.

The oily material thus obtained was identified as a desired compound by various instrumental analysis.

(3) Synthesis of N-n-propyl 4-(p-toluenesulfonylaminocarbonylamino)benzamide.

The procedure in Synthesis Example 13 (3) was repeated except that 5.8 g of N-n-propyl 3-aminobenzamide was replaced by 5.8 g of N-n-propyl 4-aminobenzamide. Thus, 10.8 g of a product was obtained as white crystals.

The analytical values of the product in the form of white crystals were identified as those of a desired compound by various instrumental analysis.

Synthesis Example 18

Synthesis of N-n-octyl 4-(p-toluenesulfonylamino carbonylamino)benzamide.

(1) Synthesis of raw material, i.e., N-n-octyl 4-nitrobenzamide.

The procedure in Synthesis Example 13 (1) was repeated except that 3-nitrobenzoyl chloride was replaced by 4-nitrobenzoyl chloride and that 3.0 g of n-propylamine was replaced by 6.6 g of n-octylamine. Thus, 10.6 g of a product was obtained as white crystals.

The product in the form of white crystals was identified as a desired compound by various instrumental analysis.

(2) Synthesis of N-n-octyl 4-aminobenzamide.

The procedure in Synthesis Example 13 (2) was repeated except that 7.7 g of N-n-propyl 3-nitrobenzamide was replaced by 10.3 g of N-n-octyl 4-nitrobenzamide. Thus, 9.3 g of a product was obtained as white crystals.

The product in the form of white crystals was identified as a desired compound by various instrumental analysis.

(3) Synthesis of N-n-octyl 4-(p-toluenesulfonylaminocarbonylamino)benzamide.

The procedure in Synthesis Example 13 (3) was repeated except that 5.8 g of N-n-propyl 3-aminobenzamide was replaced by 8.1 g of N-n-octyl 4-aminobenzamide. Thus, 11.3 g of a product was obtained as white crystals.

The analytical values of the product in the form of white crystals were identified as those of a desired compound by various instrumental analysis.

Example 1

A thermosensitive recording sheet was prepared by following the procedure shown below:

(1) Preparation of Pigment-coated Paper

To a dispersion prepared by dispersing 85 parts of calcined clay (ANSILEXT™ made by Engelhard Minerals Corporation) in 320 parts of water, 40 parts of a styrene/butadiene copolymer emulsion (solid content: 50%) and 50 parts of a 10% aqueous solution of oxidized starch were added to prepare a coating liquid. The coating liquid thus prepared was coated on a support sheet with a basis weight of 48 g/m$^2$ so that the coating amount was 7.0 g/m$^2$ after the coating liquid was dried. Thus, a pigment-undercoated sheet was obtained.

(2) Preparation of Dispersion "A"

| Components | Amount (part(s)) |
|---|---|
| 3-(N,N-dibutylamino)-6-methyl-7-anilinofluoran | 20 |
| 10% solution of polyvinyl alcohol | 10 |
| Water | 70 |

The above-mentioned composition was ground using a sand grinder until the average particle diameter reached 1 µm or less.

(3) Preparation of Dispersion "B"

| Components | Amount (part(s)) |
|---|---|
| 3-p-toluenesulfonylpropyl 4-p-toluenesulfonyl-aminocarbonylaminobenzoate (Chmical formula XI) | 20 |
| 10% solution of polyvinyl alcohol | 10 |
| Water | 70 |

The above-mentioned composition was ground using a sand grinder until the average particle diameter reached 1 µm or less.

(4) Preparation of Dispersion "C"

| Components | Amount (part(s)) |
|---|---|
| Di-p-methylbenzyl oxalate | 20 |
| 10% solution of polyvinyl alcohol | 10 |

The above-mentioned composition was ground using a sand grinder until the average particle diameter reached 1 µm or less.

(5) Formation of Recording Layer

A mixture of 60 parts of the above-mentioned dispersion "A," 120 parts of the dispersion "B," 120 parts of the dispersion "C," 23 parts of a kaolinite pigment (HG CLAY™ made by J. M Huber Corporation), 20 parts of a 25% dispersion of zinc stearate, 15 parts of a 30% paraffin dispersion, and 120 parts of a 10% aqueous solution of polyvinyl alcohol was stirred to prepare a coating liquid. The coating liquid thus prepared was coated on one surface of the pigment-coated paper and dried so that the coating amount was 5.0 g/m$^2$ after drying, whereby a thermosensitive recording layer was formed. A thermosensitive recording sheet was thus obtained.

(6) Supercalendering

The thermosensitive recording sheet thus obtained was subjected to supercalendering so as to have a surface smoothness of 800 to 1000 sec in terms of Bekk smoothness.

(7) A Variety of Tests (a) Brightness (Whiteness)

The brightness of the above-mentioned thermosensitive recording sheet sample was measured using a Hunter brightness meter (made by Toyo Seiki Seisaku-Sho, Ltd.).

(b) Coloring Test

In a sample of the thermosensitive recording sheet color development was caused in a checked pattern under such printing conditions that the applied pulse width was 1.0 ms using a dynamic thermosensitive coloring simulator "THPMD" (applied voltage: 21.7 V), made by Okura Electric Company. The coloring density was measured using a Macbeth reflection type densitometer RD-914. The recording sensitivity is represented by the coloring density.

(c) Heat Resistance Test for Evaluating Coloring of White Background Portion

A sample of the above-mentioned thermosensitive recording sheet was placed in a thermostatic chamber of 60° C. for 24 hours. The density of a white background portion was measured in the same manner as in the aforementioned test (b).

(d) Moisture Resistance Test for Evaluating Coloring of White Background Portion A sample of the above-mentioned thermosensitive recording sheet was placed in a thermo-hygrostat of 40° C. and 90%RH for 24 hours. The density of a white background portion was measured in the same manner as in the aforementioned test (b).

The results of the above-mentioned tests (a), (b), (c) and (d) are shown in TABLE 1.

Example 2

The procedure in Example 1 was repeated except that 3-p-toluenesulfonylpropyl 4-p-toluenesulfonylaminocarbonylaminobenzoate was replaced by N-3-(3-p-toluenesulfonylaminocarbonylaminobenzoyloxy)propylphthalimide (Chemical formula (XIII)) in the preparation of the dispersion "B." The results of the tests are shown in TABLE 1.

Example 3

The procedure in Example 1 was repeated except that 3-p-toluenesulfonylpropyl 4-p-toluenesulfonylaminocarbonylaminobenzoate was replaced by 4-[4-(4-iso-propoxyphenylsulfonyl)phenoxy)]butyl 4-p-toluenesulfonylaminocarbonylaminobenzoate (Chemical formula (XII)) in the preparation of the dispersion "B." The results of the tests are shown in TABLE 1.

Example 4

The procedure in Example 1 was repeated except that 3-p-toluenesulfonylpropyl 4-p-toluenesulfonylaminocarbonylaminobenzoate was replaced by N-phenyl-N 3-(4-p-toluenesulfonylaminocarbonylaminobenzoyloxy)propylurea (Chemical formula (XIV)) in the preparation of the dispersion "B." The results of the tests are shown in TABLE 1.

Example 5

The procedure in Example 1 was repeated except that 3-p-toluenesulfonylpropyl 4-p-toluenesulfonylaminocarbonylaminobenzoate was replaced by butyl 4-p-toluenesulfonylaminocarbonylaminobenzenesulfonate in the preparation of the dispersion "B." The results of the tests are shown in TABLE 1.

Example 6

The procedure in Example 1 was repeated except that 3-p-toluenesulfonylpropyl 4-p-toluenesulfonylaminocarbonylaminobenzoate was replaced by dipropyl 4-p-toluenesulfonylaminocarbonylaminobenzene phosphonate in the preparation of the dispersion "B." The results of the tests are shown in TABLE 1.

Comparative Example 1

The procedure in Example 1 was repeated except that 3-p-toluenesulfonylpropyl 4-p-toluenesulfonylaminocarbonylaminobenzoate was replaced by 2,2-bis(4-hydroxyphenyl)propane (bisphenol A) in the preparation of the dispersion "B."

The results of the tests (a), (b), (c) and (d) for checking the requirements for the thermosensitive recording material are shown in TABLE 1.

TABLE 1

| | Brightness | Coloring Density (D) (1.0 ms) | Background Densitiy (D) after Moisture Resistance Test | Background Density (D) after Heat Resistance Test |
| --- | --- | --- | --- | --- |
| Example 1 | 80.8 | 1.38 | 0.07 | 0.07 |
| Example 2 | 81.2 | 1.35 | 0.06 | 0.06 |
| Example 3 | 80.4 | 1.36 | 0.07 | 0.07 |
| Example 4 | 80.1 | 1.37 | 0.07 | 0.07 |
| Example 5 | 80.2 | 1.34 | 0.07 | 0.07 |
| Example 6 | 80.5 | 1.34 | 0.07 | 0.07 |
| Comparative Example 1 | 77.9 | 1.33 | 0.14 | 0.12 |

As is apparent from TABLE 1, the thermosensitive recording materials of the present invention are provided with basic properties required for the thermosensitive recording material. To be more specific, the thermosensitive recording materials of the present invention can exhibit high brightness (whiteness) and high color development performance, with coloring of the white background portion being prevented under the circumstances of high temperature and humidity.

Example 7

A thermosensitive recording sheet was prepared by following the procedure shown below.

(1) Preparation of Pigment-coated Paper

A pigment-coated paper was obtained in the same manner as in Example 1 (1).

(2) Preparation of Dispersion "A"

| Components | Amount (part(s)) |
| --- | --- |
| 3-(N,N-dipentylamino)-6-methyl-7-anilinofluoran | 10 |
| Di-p-methylbenzyl oxalate | 8 |
| Di-p-chlorbenzyl oxalate | 2 |
| 10% solution of polyvinyl alcohol | 10 |
| Water | 70 |

The above-mentioned composition was ground using a sand grinder until the average particle diameter reached 1 μm or less.

(3) Preparation of Dispersion "B"

| Components | Amount (part(s)) |
| --- | --- |
| 3-p-toluenesulfonylpropyl 4-p-toluenesulfonyl-aminocarbonylaminobenzoate (Chemical formula XI) | 30 |
| 10% solution of polyvinyl alcohol | 10 |
| Water | 70 |

The above-mentioned composition was ground using a sand grinder until the average particle diameter reached 1 μm or less.

(5) Formation of Recording Layer

A mixture of 20 parts of the above-mentioned dispersion "A," 30 parts of the dispersion "B." 40 parts of a 50% kaolinite pigment (HG CLAY™ made by J. M Huber Corporation), 3 parts of a 35% dispersion of zinc stearate, and 8 parts of a 10% aqueous solution of polyvinyl alcohol was stirred to prepare a coating liquid. The coating liquid thus prepared was coated on one surface of the pigment-coated paper and dried so that the coating amount was 5.0 g/m² after drying, whereby a thermosensitive recording layer was formed. A thermosensitive recording sheet was thus obtained.

(7) A Variety of Tests (e) High Heat Resistance Test for Evaluating Coloring of Background.

In a sample of the thermosensitive recording sheet thus obtained, color development was caused in a checked pattern under such printing conditions that the applied pulse width was 1.0 ms using a dynamic thermosensitive coloring simulator "THPMD" (applied voltage: 21.7 V), made by Okura Electric Company. The sample was then placed in a thermostatic chamber of 100° C. for one hour, and thereafter the density of a background portion was measured using a Macbeth reflection type densitometer RD-914. In addition, the contrast between a recorded portion and a background portion was visually observed.

The results of the high heat resistance test (e) for evaluating coloring of background are shown in TABLE 2, and the results of plasticizer resistance test (f) are shown in TABLE 3.

Example 8

The procedure in Example 7 was repeated except that 3-p-toluenesulfonylpropyl 4-p-toluenesulfonylaminocarbonylaminobenzoate was replaced by N-3-(3-p-toluenesulfonylaminocarbonylaminobenzoyloxy) propylphthalimide (Chemical formula (XIII)) in the preparation of the dispersion "B." The results of the tests are shown in TABLE 2.

Example 9

The procedure in Example 7 was repeated except that 3-p-toluenesulfonylpropyl 4-p-toluenesulfonylaminocarbonylaminobenzoate was replaced by 4-[4-(4-iso-propoxyphenylsulfonyl)phenoxy)]butyl 4-p-toluenesulfonylaminocarbonylaminobenzoate (Chemical formula (XII)) in the preparation of the dispersion "B." The results of the tests are shown in TABLE 2.

Example 10

The procedure in Example 7 was repeated except that 3-p-toluenesulfonylpropyl 4-p-toluenesulfonylaminocarbonylaminobenzoate was replaced by N-phenyl-N 3-(4-p-toluenesulfonylaminocarbonylamino benzoyloxy)propylurea (Chemical formula (XIV)) in the preparation of the dispersion "B." The results of the tests are shown in TABLE 2.

Example 11

The procedure in Example 7 was repeated except that 3-p-toluenesulfonylpropyl 4-p-toluenesulfonylaminocarbonylaminobenzoate was replaced by butyl 4-p-toluenesulfonylaminocarbonylaminobenzenesulfonate in the preparation of the dispersion "B." The results of the tests are shown in TABLE 2.

Example 12

The procedure in Example 7 was repeated except that 3-p-toluenesulfonylpropyl 4-p-toluenesulfonylaminocarbonylaminobenzoate was replaced by dipropyl 4-p-toluenesulfonylaminocarbonylaminobenzene phosphonate in the preparation of the dispersion "B." The results of the tests are shown in TABLE 2.

Comparative Example 2

The procedure in Example 7 was repeated except that 3-p-toluenesulfonylpropyl 4-p-toluenesulfonylaminocarbonylaminobenzoate was replaced by p-toluenesulfonylaminocarbonylaminobenzene in the preparation of the dispersion "B." The results of the tests are shown in TABLE 2.

Comparative Example 3

The procedure in Example 7 was repeated except that 3-p-toluenesulfonylpropyl 4-p-toluenesulfonylaminocarbonylaminobenzoate was replaced by butyl p-toluenesulfonylaminocarbonylaminobenzoate in the preparation of the dispersion "B." The results of the tests are shown in TABLE 2.

Comparative Example 4

The procedure in Example 7 was repeated except that 3-p-toluenesulfonylpropyl 4-p-toluenesulfonylaminocarbonylaminobenzoate was replaced by 2,2-bis(4-hyrdoxyphenyl)propane (bisphenol A) in the preparation of the dispersion "B." The results of the tests are shown in TABLE 2.

TABLE 2

| | Coloring Density (1.0 ms) (D) | Density of White Background (D) Before heat resistance test | Density of White Background (D) After high heat resistance test | Printing Contrast |
|---|---|---|---|---|
| Example 7 | 1.42 | 0.07 | 0.42 | Excellent |
| Example 8 | 1.38 | 0.07 | 0.63 | Good |
| Example 9 | 1.39 | 0.07 | 0.51 | Excellent |
| Example 10 | 1.40 | 0.07 | 0.61 | Good |
| Example 11 | 1.39 | 0.07 | 0.55 | Excellent |
| Example 12 | 1.38 | 0.07 | 0.53 | Excellent |
| Comparative Example 2 | 1.40 | 0.07 | 1.02 | Poor |
| Comparative Example 3 | 1.39 | 0.07 | 1.07 | Poor |
| Comparative Example 4 | 1.41 | 0.07 | 1.12 | Poor |

As shown in TABLE 2, coloring of the background considerably takes place in the thermosensitive recording sheets of Comparative Examples 2, 3 and 4 to make recorded images illegible under the circumstances of high temperature, equivalent to temperature in cars under the blazing sun in summer. In contrast to this, it is possible to satisfactorily read recorded images in Examples 7 and 8 where the color developers according to the present invention are employed.

(f) Plasticizer Resistance Test

Each of the thermosensitive recording sheet samples of Examples 7, 8, 9, 10, 11 and 12 subjected to color development at the applied pulse width of 1.0 ms in the same manner as in the high heat resistance test (e) for evaluating coloring of background was interposed between two vinyl chloride films made by Mitsubishi Plastics Industries Limited (which vinyl chloride films belong to a group of wrapping plastic films with the highest content of plasticizers). Under load of 10 gf/cm$^2$, each thermosensitive recording sheet sample was allowed to stand in a thermostatic chamber of 40° C. for 17 hours. After that the vinyl chloride films were peeled away and the density of a remaining image was measured using a Macbeth reflection type densitometer. The image retention ratio was calculated in accordance with the following formula. Further, the contrast between a recorded portion and a background portion was visually evaluated.

Image Retention Ratio (%)=[Density after Plasticizer Resistance Test/Initial Density]×100

The results are shown in TABLE 3.

Comparative Example 5

The procedure in Example 7 was repeated except that 3-p-toluenesulfonylpropyl 4-p-toluenesulfonylaminocarbonylaminobenzoate was replaced by 2,2-bis(4-hyrdoxyphenyl)propane (bisphenol A) in the preparation of the dispersion "B." The results are shown in TABLE 3.

TABLE 3

| | Density of White Background (D) | Initial Density of Recorded Image (1.0 ms) (D) | Image Retnention Ratio after Plasticizer Resistance Test (%) | Printing Contrast |
|---|---|---|---|---|
| Example 7 | 0.07 | 1.42 | 93 | Excellent |
| Example 8 | 0.07 | 1.38 | 77 | Good |
| Example 9 | 0.07 | 1.39 | 81 | Excellent |
| Example 10 | 0.07 | 1.40 | 76 | Good |
| Example 11 | 0.07 | 1.39 | 86 | Excellent |
| Example 12 | 0.07 | 1.38 | 84 | Excellent |
| Comparative Example 5 | 0.10 | 1.40 | 18 | Poor |

As is apparent from TABLE 3, recorded images fade away and become unreadable by contact with the vinyl chloride films in Comparative Example 5. However, recorded images are retained to be read easily in Examples 7, 8, 9, 10, 11 and 12 where the color developers of the present invention are employed.

In the above, 3-p-toluenesulfonylpropyl 4-p-toluenesulfonylamino carbonylaminobenzoate represented by chemical formula (XI), 4-[4-(4-isopropoxyphenylsulfonyl)phenoxy)]butyl 4-p-toluenesulfonylaminocarbonyl aminobenzoate represented by chemical formula (XII), N-3-(3-p-toluenesulfonylaminocarbonylaminobenzoyloxy) propylphthalimide represented by chemical formula (XIII), and N-phenyl-N'-3-(4-p-toluenesulfonylaminocarbonylaminobenzoyloxy) propylurea represented by chemical formula (XIV) are compounds, each structure of which compounds was definitely determined by various analysis.

Example 13

A thermosensitive recording sheet was prepared by following the procedure shown below.

(1) Preparation of Pigment-coated Paper

To a dispersion prepared by dispersing 85 parts of calcined clay (ANSILEX™ in 320 parts of water, 40 parts of a styrene/butadiene copolymer emulsion (solid content: 50%), and 50 parts of a 10% aqueous solution of oxidized starch were added to prepare a coating liquid. The coating liquid thus prepared was coated on a support sheet with a basis weight of 48 g/m$^2$ so that the coating amount was 7.0 g/m$^2$ after the coating liquid was dried. Thus, a pigment-coated paper was obtained.

(2) Preparation of Dispersion "A"

| Components | Amount (part(s)) |
|---|---|
| 3-(N,N-dipentylamino)-6-methyl-7-anilinofluoran | 20 |
| 10% solution of polyvinyl alcohol | 10 |
| Water | 70 |

The above-mentioned composition was ground using a sand grinder until the average particle diameter reached 1 μm or less.

(3) Preparation of Dispersion "B"

| Components | Amount (part(s)) |
| --- | --- |
| Butyl 3-(p-toluenesulfonylamino-carbonylamino)benzoate | 20 |
| 10% solution of polyvinyl alcohol | 10 |
| Water | 70 |

The above-mentioned composition was ground using a sand grinder until the average particle diameter reached 1 μm or less.

(4) Preparation of Dispersion "C"

| Components | Amount (part(s)) |
| --- | --- |
| Di-p-methylbenzyl oxalate | 20 |
| 10% solution of polyvinyl alcohol | 10 |
| Water | 70 |

The above-mentioned composition was ground using a sand grinder until the average particle diameter reached 1 μm or less.

(5) Formation of Recording Layer

A mixture of 60 parts of the above-mentioned dispersion "A," 120 parts of the dispersion "B," 120 parts of the dispersion "C," 23 parts of a kaolinite pigment (HG CLAY™ made by J. M Huber Corporation), 20 parts of a 25% dispersion of zinc stearate, 15 parts of a 30% paraffin dispersion, and 120 parts of a 10% aqueous solution of polyvinyl alcohol was stirred to prepare a coating liquid. The coating liquid thus prepared was coated on one surface of the pigment-coated paper and dried so that the coating amount was 5.0 g/m² after drying, whereby a thermosensitive coloring layer was formed. A thermosensitive recording sheet was thus obtained.

(6) Supercalendering

The thermosensitive recording sheet thus obtained was subjected to supercalendering so as to have a surface smoothness of 800 to 1000 sec.

(7) A Variety of Tests (a) Brightness

The degree of brightness(whiteness) of the above-mentioned thermosensitive recording sheet sample was measured using a Hunter brightness meter (made by Toyo Seiki Seisaku-Sho, Ltd.).

(b) Coloring Test

In a sample of the thermosensitive recording sheet color development was caused in a checked pattern under such printing conditions that the applied pulse width was 1.0 ms using a dynamic thermosensitive coloring simulator "THPMD" (applied voltage: 21.7 V), made by Okura Electric Company. The coloring density was measured using a Macbeth reflection type densitometer RD-914. The recording sensitivity is represented by the coloring density.

(c) Moisture Resistance Test for Evaluating Coloring of White Background Portion A sample of the thermosensitive recording sheet was placed in a thermo-hygrostat of 40° C. and 90%RH for 24 hours. The density of a white background portion was measured in the same manner as in the aforementioned test (b) The results of the above-mentioned tests (a), (b) and (c) are shown in TABLE 4.

Example 14

The procedure in Example 13 was repeated except that butyl 3-(p-toluenesulfonylaminocarbonylamino)benzoate was replaced by propyl 3-(p-toluenesulfonylaminocarbonylamino)benzoate in the preparation of the dispersion "B." The results of the tests are shown in TABLE 4.

Example 15

The procedure in Example 13 was repeated except that butyl 3-(p-toluenesulfonylaminocarbonylamino)benzoate was replaced by methyl 3-(p-toluenesulfonylaminocarbonylamino)benzoate in the preparation of the dispersion "B." The results of the tests are shown in TABLE 4.

Example 16

The procedure in Example 13 was repeated except that butyl 3-(p-toluenesulfonylaminocarbonylamino)benzoate was replaced by ethyl 3-(p-toluenesulfonylaminocarbonylamino)benzoate in the preparation of the dispersion "B." The results of the tests are shown in TABLE 4.

Example 17

The procedure in Example 13 was repeated except that butyl 3-(p-toluenesulfonylaminocarbonylamino)benzoate was replaced by octyl 3-(p-toluenesulfonylaminocarbonylamino)benzoate in the preparation of the dispersion "B."

In addition to the above-mentioned tests (a) to (c), the following test (d) was carried out.

(d) Plasticizer Resistance Test

One of the representative plasticizers, dioctyl terephthalate, was applied to the thermosensitive recording sheet sample subjected to color development at the applied pulse width of 1.0 ms in the test (b) within 30 minutes after the color development. The sample was allowed to stand at room temperature for 3 hours. After an excess of oil or plasticizer was wiped from the sample, the density of a remaining image was measured using a Macbeth reflection type densitometer. The image retention ratio was calculated in accordance with the following formula.

Image Retention Ratio (%)=[Density after Plasticizer Resistance Test/Initial Density]×100

The results of the tests (a), (b), (c) and (d) are shown in TABLE 5.

Example 18

The procedure in Example 17 was repeated except that octyl 3-(p-toluenesulfonylaminocarbonylamino)benzoate was replaced by dodecyl 3-(p-toluenesulfonylaminocarbonylamino)benzoate in the preparation of the dispersion "B." The results of the tests are shown in TABLE 5.

Example 19

The procedure in Example 17 was repeated except that octyl 3-(p-toluenesulfonylaminocarbonylamino)benzoate was replaced by octadecyl 3-(p-toluenesulfonylaminocarbonylamino)benzoate in the preparation of the dispersion "B." The results of the tests are shown in TABLE 5.

Comparative Example 6

The procedure in Example 17 was repeated except that octyl 3-(p-toluenesulfonylaminocarbonylamino)benzoate was replaced by 2,2-bis(4-hydroxyphenyl)propane (bisphenol A) in the preparation of the dispersion "B." The results of the tests are shown in TABLE 4 and TABLE 5.

Comparative Example 7

The procedure in Example 17 was repeated except that octyl 3-(p-toluenesulfonylaminocarbonylamino)benzoate was replaced by propyl 4-(p-toluenesulfonylaminocarbonylamino)benzoate in the preparation of the dispersion "B." The results of the tests are shown in TABLE 4 and TABLE 5.

TABLE 4

|  | Coloring Density (1.0 ms) (D) | Brightness | White Background Density after Moisture Resistance Test |
| --- | --- | --- | --- |
| Example 13 | 1.35 | 84.3 | 0.05 |
| Example 14 | 1.33 | 84.2 | 0.05 |
| Example 15 | 1.32 | 83.5 | 0.06 |
| Example 16 | 1.34 | 84.5 | 0.06 |
| Comparative Example 6 | 1.33 | 77.9 | 0.11 |
| Comparative Example 7 | 1.28 | 83.5 | 0.06 |

TABLE 5

|  | Coloring Density (1.0 ms) (D) | Brightness | White Background Density after Moisture Resistance Test | Retention Ratio after Application of Plasticizer (%) |
| --- | --- | --- | --- | --- |
| Example 17 | 1.35 | 83.8 | 0.06 | 83 |
| Example 18 | 1.33 | 83.6 | 0.06 | 85 |
| Example 19 | 1.40 | 82.1 | 0.06 | 86 |
| Comparative Example 6 | 1.33 | 77.9 | 0.11 | 18 |
| Comparative Example 7 | 1.28 | 83.5 | 0.06 | 30 |

As can be seen from the above-mentioned TABLE 4 and TABLE 5, the thermosensitive recording materials of the present invention can exhibit high brightness(whiteness), with coloring of a white background portion being minimized under the circumstances of high temperature and humidity, and exhibit excellent color development performance and high plasticizer resistance. In particular, the plasticizer resistance is remarkably improved when $R_8$ has 5 or more carbon atoms in the color developer of general formula (IV).

Example 20

A thermosensitive recording sheet was prepared by following the procedure shown below.

(1) Preparation of Pigment-coated Paper

To a dispersion prepared by dispersing 85 parts of calcined clay (ANSILEX™ made by Engelhard Minerals Corporation) in 320 parts of water, 40 parts of a styrene/butadiene copolymer emulsion (solid content: 50%), and 50 parts of a 10% aqueous solution of oxidized starch were added to prepare a coating liquid. The coating liquid thus prepared was coated on a support sheet with a basis weight of 48 g/m² so that the coating amount was 7.0 g/m² after the coating liquid was dried. Thus, a pigment-coated paper was obtained.

(2) Preparation of Dispersion "A"

| Components | Amount (part(s)) |
| --- | --- |
| 3-di(n-pentyl)amino-6-methyl-7-anilinofluoran | 10 |
| Di-p-methybenzyl oxalate | 8 |
| Di-p-chlorobenzyl oxalate | 2 |
| Water-soluble polymer "Metolose 60SH03" ™ (made by Shin-Etsu Chemical Co., Ltd. | 10 |
| Water | 70 |

The above-mentioned composition was ground using a sand grinder until the average particle diameter reached 1 μm or less.

(3) Preparation of Dispersion "B"

| Components | Amount (part(s)) |
| --- | --- |
| N-n-propyl 3-(p-toluenesulfonylamino-carbonyl-amino)benzamide | 20 |
| 10% solution of polyvinyl alcohol | 10 |
| Water | 70 |

The above-mentioned composition was ground using a sand grinder until the average particle diameter reached 1 μm or less.

(4) Formation of Recording Layer

A mixture of 20 parts of the above-mentioned dispersion "A," 30 parts of the dispersion "B," 30 parts of a kaolinite pigment (HG CLAY™ made by J.M Huber Corporation), 5 parts of a 36% dispersion of zinc stearate, and 15 parts of a 10% aqueous solution of polyvinyl alcohol was stirred to prepare a coating liquid. The coating liquid thus prepared was coated on one surface of the pigment-coated paper and dried so that the coating amount was 5.0 g/m² after drying, whereby a thermosensitive coloring layer was formed. A thermosensitive recording sheet was thus obtained.

(5) Supercalendering

The thermosensitive recording sheet thus obtained was subjected to supercalendering so as to have a surface smoothness of 800 to 1000 sec.

(6) A Variety of Tests (a) Brightness(Whiteness)

The brightness of the above-mentioned thermosensitive recording sheet sample was measured using a Hunter brightness meter (made by Toyo Seiki Seisaku-Sho, Ltd.).

(b) Coloring Test

In a sample of the thermosensitive recording sheet color development was caused in a checked pattern under such printing conditions that the applied pulse width was 1.0 ms using a dynamic thermosensitive coloring simulator "THPMD" (applied voltage: 21.7 V), made by Okura Electric Company. The coloring density was measured using a Macbeth reflection type densitometer RD-914. The recording sensitivity is represented by the coloring density.

(c) Heat Resistance Test for Evaluating Coloring of White Background Portion

A sample of the above-mentioned thermosensitive recording sheet was placed in a thermostatic chamber of 100° C. for one hour. The density of a white background portion was measured in the same manner as in the aforementioned test (b).

(d) Heat Resistance Test for Evaluating Decolorization of Image Recorded Portion The thermosensitive recording sheet sample subjected to color development at the applied pulse width of 1.0 ms in the test (b) was placed in a thermostatic chamber of 100° C. for one hour. The density of a recorded portion was measured in the same manner as in the aforementioned test (b).

The results of the above-mentioned tests (a), (b), (c) and (d) are shown in TABLE 6.

Example 21

The procedure in Example 20 was repeated except that N-n-propyl 3-(p-toluenesulfonylaminocarbonylamino)benzamide was replaced by N-n-butyl 3-(p-toluenesulfonylaminocarbonylamino)benzamide in the preparation of the dispersion "B." The results of the tests are shown in TABLE 6.

Example 22

The procedure in Example 20 was repeated except that N-n-propyl 3-(p-toluenesulfonylaminocarbonylamino)benzamide was replaced by N-n-octyl 3-(p-toluenesulfonylaminocarbonylamino)benzamide in the preparation of the dispersion "B." The results of the tests are shown in TABLE 6.

Comparative Example 8

The procedure in Example 20 was repeated except that N-n-propyl 3-(p-toluenesulfonylaminocarbonylamino)benzamide was replaced by 2,2-bis(4-hydroxypheny)propane (bisphenol A) in the preparation of the dispersion "B." The results of the tests are shown in TABLE 6.

Comparative Example 9

The procedure in Example 20 was repeated except that N-n-propyl 3-(p-toluenesulfonylaminocarbonylamino)benzamide was replaced by N-(p-toluenesulfonyl)-N phenylurea in the preparation of the dispersion "B." The results of the tests are shown in TABLE 6.

TABLE 6

|  | Coloring Density (1.0 ms) (D) | Brightness | Density of White Background Heat Resistance Test | Density of Recorded Image after Heat Resistance Test |
|---|---|---|---|---|
| Example 20 | 1.44 | 83.0 | 0.20 | 1.40 |
| Example 21 | 1.45 | 83.3 | 0.25 | 1.39 |
| Example 22 | 1.43 | 82.9 | 0.49 | 1.35 |
| Comparative Example 8 | 1.40 | 79.1 | 0.88 | 0.95 |
| Comparative Example 9 | 1.40 | 82 | 1.07 | 1.15 |

As is apparent from the above TABLE 6, the thermosensitive recording materials according to the present invention can exhibit high brightness (whiteness) and excellent color development properties, with neither coloring of a white background portion, nor decolorization of a recorded image under the circumstances of high temperature.

The thermosensitive recording material of the present invention comprises at least one member selected from the organic compounds represented by general formulas (I), (II) and (III) as the color developer in the thermosensitive coloring layer. Therefore, the thermosensitive recording material can exhibit high brightness and excellent color development performance, and further, high preservability of colored images with minimum coloring of the background under the circumstances of high temperature and humidity, in particular, under severe environmental conditions equivalent to the case where the recording material is placed in vehicles under the blazing sun in summer or in microwave ovens for cooking by the application of heat. In the case where the thermosensitive recording material of the present invention comprises at least one member selected from the organic compounds represented by general formulas (I), (II) and (III) as the color developer in the thermosensitive coloring layer, the preservation stability of the colored images is remarkably high even when the recording material comes into contact with plasticizers and vinyl chloride films.

The present invention provides a thermosensitive recording material with excellent preservation stability of recording, with no decolorization of images being caused if once colored, and high recording sensitivity. The thermosensitive recording material of the present invention exhibits long-term preservation stability of recording, and at the same time, excellent environmental resistance such as heat resistance of recorded images, in particular, the resistance to higher temperature, on the assumption that the recording material is placed in vehicles under the blazing sun in summer or in microwave ovens for cooking by the application of heat, and moisture resistance, and in addition, excellent chemical resistance such as oil resistance and plasticizer resistance, and high recording sensitivity and whiteness. The thermosensitive recording material is therefore useful for paper for cash dispenser, passenger tickets, passes, parking tickets, admission tickets, commutation tickets, labels such as POS labels, and cards such as pre-paid cards.

The heat resistance and the plasticizer resistance are remarkably excellent in particular when the thermosensitive recording material of the present invention comprises as the color developer an organic compound of general formula (I) where $Z_1$ is sulfonyl group substituted with at least one member selected from the group consisting of an alkyl group, an aryl group, and an aralkyl group, or $Z_1$ is a cyclic imido group with a nitrogen atom in the cyclic imido group being bonded to $Y_1$, or $Z_1$ is urea group.

When the thermosensitive recording material comprises an aromatic compound represented by formula (IV) as the color developer in the thermosensitive recording layer, the brightness is high, the white background can be prevented from coloring under the circumstances of high temperature and humidity, and the colored images can show high image preservability and high coloring density.

The above-mentioned thermosensitive recording material of the present invention exhibits excellent preservation stability of recording, with no decolorization of images being caused if once colored, and high recording sensitivity. The thermosensitive recording material of the present invention exhibits excellent long-term preservation stability of recording, and at the same time, high environmental resistance such as heat resistance and moisture resistance of recorded images, and high oil resistance and plasticizer resistance. In addition to the above, the recording sensitivity and high brightness, so that the thermosensitive recording material is advantageously used as image recording paper, paper for cash dispenser, passenger tickets, passes, commutation tickets, labels such as POS labels, cards such as pre-paid cards, and passes.

The plasticizer resistance is particularly improved when $R_8$ in general formula (IV) has 5 or more carbon atoms.

In the thermosensitive recording material, when a sulfonyl(thio)urea compound represented by formula (V) is used as the color developer in the thermosensitive coloring layer, the brightness(whiteness) is high and the colored images show high recording sensitivity and high coloring density. The above-mentioned thermosensitive recording material exhibits excellent long-term preservation stability of recording and high environmental resistance such as heat resistance and moisture resistance of recorded images, and high oil resistance. Further, the thermosensitive recording material is provided with excellent image preservability and image recognition performance, that is, the white background portions can be prevented from coloring and the recorded image portions can be prevented from decolorizing under the circumstances of severely high temperature, for example, even when placed in tightly sealed cars under the blazing sun in summer or in heating cookers such as microwave ovens.

What is claimed is:

1. A thermosensitive recording material comprising a sheet-shaped support and a thermosensitive recording layer which is formed on at least one surface of the support and comprises a colorless or light-colored dye precursor and a color developer capable of reacting with the dye precursor and inducing color formation therein upon application of heat thereto, the color developer comprising at least one compound selected from the group consisting of compounds represented by general formulas (I) to (V):

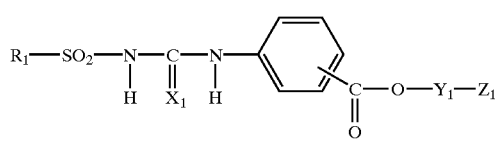
(I)

wherein $R_1$ is at least one member selected from the group consisting of a substituted or unsubstituted aromatic hydrocarbon group and a substituted or unsubstituted aliphatic (and alicyclic) hydrocarbon group; $X_1$ is oxygen atom or sulfur atom; $Y_1$ is a bivalent group having 2 or more carbon atoms; $Z_1$ is a monovalent group having at least one hetero atom, provided that $Z_1$ is not a group including sulfonylurea group (—$SO_2NHCONH$—); and benzene ring has at least one —$COOY_1Z_1$ group, provided that a plurality of —$COOY_1Z_1$ groups may be the same or different when there are two or more;

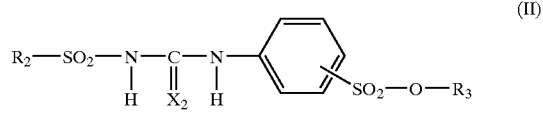
(II)

wherein $R_2$ is at least one member selected from the group consisting of a substituted or unsubstituted aromatic hydrocarbon group and a substituted or unsubstituted aliphatic (and alicyclic) hydrocarbon group; $R_3$ is a monovalent organic residue; $X_2$ is oxygen atom or sulfur atom; and benzene ring has at least one —$SO_2OR_3$ group, provided that a plurality of —$SO_2OR_3$ groups may be the same or different when there are two or more;

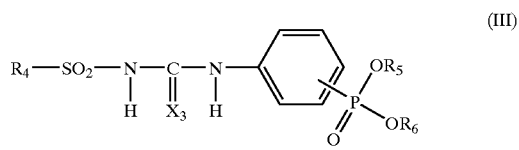
(III)

wherein $R_4$ is at least one member selected from the group consisting of a substituted or unsubstituted aromatic hydrocarbon group and a substituted or unsubstituted aliphatic (and alicyclic) hydrocarbon group; $R_5$ and $R_6$ are each independently a monovalent organic residue; $X_3$ is oxygen atom or sulfur atom; and benzene ring has at least one —$PO_3(R_5)(R_6)$ group, provided that a plurality of —$PO_3(R_5)(R_6)$ groups may be the same or different when there are two or more;

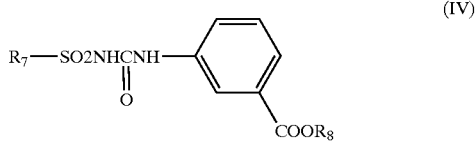
(IV)

wherein $R_7$ is at least one member selected from the group consisting of an unsubstituted aromatic ring group and a substituted aromatic ring group having at least one member selected from the group consisting of methyl group and chlorine atom; $R_8$ is one member selected from the group consisting of an alkyl group, an aralkyl group, an unsubstituted aromatic ring group, and a substituted aromatic ring group; and benzene ring has at least one —$COOR_8$ group, provided that a plurality of —$COOR_8$ groups may be the same or different when there are two or more; and

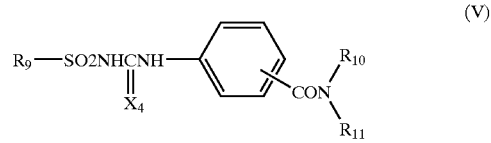
(V)

wherein $X_4$ is oxygen atom or sulfur atom; $R_9$ is a member selected from the group consisting of an unsubstituted aromatic ring group and a substituted aromatic ring group having at least one member selected from the group consisting of an alkyl group, an alkoxyl group, and a halogen atom; $R_{10}$ and $R_{11}$ are each independently a member selected from the group consisting of a hydrogen atom, an alkyl group, an aralkyl group, a group prepared by substituting a part of an alkyl moiety of the aralkyl group with a hetero atom, and a substituted or unsubstituted aromatic ring group; and benzene ring has at least one —$CONR_{10}(R_{11})$ group, provided that a plurality of —$CONR_{10}(R_{11})$ groups may be the same or different when there are two or more.

2. The thermosensitive recording material as claimed in claim 1, wherein the color developer comprises a compound selected from the group consisting of the compounds represented by general formulas (I) to (III).

3. The thermosensitive recording material as claimed in claim 1, wherein the color developer comprises the compound represented by general formula (IV).

4. The thermosensitive recording material as claimed in claim 1, wherein the color developer comprises the compound represented by general formula (V).

5. The thermosensitive recording material as claimed in claim 1, wherein the compound of general formula (I) is a compound represented by general formula (VI):

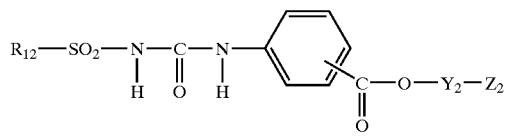

(VI)

wherein $R_{12}$ is an unsubstituted aromatic hydrocarbon group or a substituted aromatic hydrocarbon group having at least one member selected from the group consisting of an alkyl group, an alkoxyl group, and a halogen atom; $Y_2$ is a bivalent group having 2 or more carbon atoms; $Z_2$ is a substituted sulfonyl group having at least one member selected from the group consisting of an alkyl group, an aryl group, and an aralkyl group, or a substituted imido group having at least one member selected from the group consisting of an alkyl group, an aryl group, and an aralkyl group; and benzene ring has at least one —$COOY_2Z_2$ group, provided that a plurality of —$COOY_2Z_2$ groups may be the same or different when there are two or more.

6. The thermosensitive recording material as claimed in claim 1, wherein the compound of general formula (I) is at least one compound selected from the group consisting of compounds represented by general formulas (VII), (VIII) and (IX):

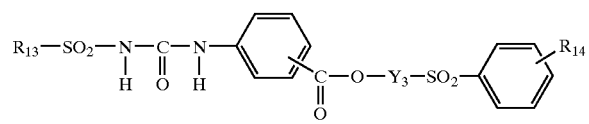

(VII)

wherein $R_{13}$ is an unsubstituted aromatic hydrocarbon group or a substituted aromatic hydrocarbon group having at least one member selected from the group consisting of methyl group, methoxy group, and chlorine atom; $R_{14}$ is a member selected from the group consisting of a hydrogen atom, chlorine atom, a nitro group, an alkyl group, an alkoxyl group, an aryl group, an aryloxy group, an aralkyl group, and an aralkyloxy group, provided that two or more members represented by $R_{14}$ may be independently bonded to a benzene ring as substituents; $Y_3$ is a bivalent group having 2 or more carbon atoms; and the other benzene ring has at least one ester group including $Y_3$, provided that a plurality of ester groups including $Y_3$ may be the same or different when there are two or more;

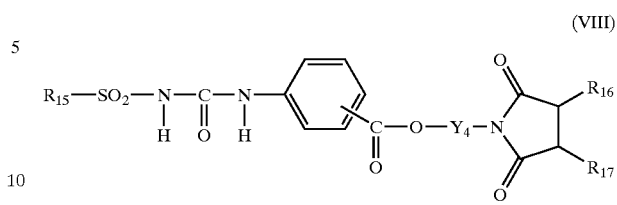

(VIII)

wherein $R_{15}$ is an unsubstituted aromatic hydrocarbon group or a substituted aromatic hydrocarbon group having at least one member selected from the group consisting of methyl group, methoxy group, and chlorine atom; $R_{16}$ and $R_{17}$ are each independently a hydrogen atom, an alkyl group, an aryl group or an aralkyl group, or $R_{16}$ and $R_{17}$ may form cyclopentane ring, cyclohexane ring, dicyclopentane ring or benzene ring in combination; $Y_4$ is a bivalent group having 2 or more carbon atoms; and benzene ring has at least one ester group including $Y_4$, provided that a plurality of ester groups including $Y_4$ may be the same or different when there are two or more; and

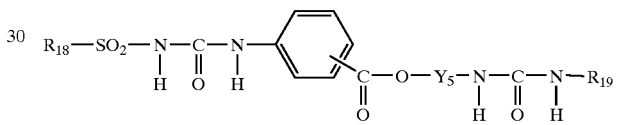

(IX)

wherein $R_{18}$ is an unsubstituted aromatic hydrocarbon group or a substituted aromatic hydrocarbon group having at least one member selected from the group consisting of methyl group, methoxy group, and chlorine atom; $R_{19}$ is a member selected from the group consisting of an alkyl group, an aryl group and an aralkyl group; $Y_5$ is a bivalent group having 2 or more carbon atoms; and benzene ring has at least one ester group including $Y_5$, provided that a plurality of ester groups including $Y_5$ may be the same or different when there are two or more.

7. The thermosensitive recording material as claimed in claim 1, wherein, in the color developer represented by general formula (V), at least one of $R_{10}$ or $R_{11}$ is a group comprising a straight-chain alkyl group, with the straight-chain alkyl moiety having 8 carbon atoms or less.

8. The thermosensitive recording material as claimed in claim 1, wherein the color developer represented by general formula (V) is a compound of general formula (X) where the —$CONR_{10}(R)_{11}$ group is at the m-position:

(X)

wherein $X_4$, $R_9$, $R_{10}$, and $R_{11}$ are each the same as defined in formula (V).

9. The thermosensitive recording material as claimed in claim 1, wherein, in the color developer represented by general formula (V), $X_4$ is oxygen atom.

10. The thermosensitive recording material as claimed in claim 8, wherein, in the color developer represented by general formula (X), $X_4$ is oxygen atom.

11. A color developer comprising at least one compound selected from the group consisting of the compounds represented by general formulas (I) to (V) as claimed in claim 1.

* * * * *